(12) United States Patent
Grates et al.

(10) Patent No.: US 10,537,335 B2
(45) Date of Patent: Jan. 21, 2020

(54) MEDICAL DISPENSING DEVICE

(71) Applicant: Covidien LP, Mansfield, MA (US)

(72) Inventors: Robert Grates, White Bear Lake, MN (US); Thomas Morley, Minneapolis, MN (US); Christopher Slaughter, Plymouth, MN (US)

(73) Assignee: Covidien LP, Mansfield, MA (US)

( * ) Notice: Subject to any disclaimer, the term of this patent is extended or adjusted under 35 U.S.C. 154(b) by 379 days.

(21) Appl. No.: 15/498,674

(22) Filed: Apr. 27, 2017

(65) Prior Publication Data
US 2018/0310943 A1 Nov. 1, 2018

(51) Int. Cl.
| | | |
|---|---|---|
| *A61B 17/12* | (2006.01) | |
| *A61M 5/315* | (2006.01) | |
| *A61M 5/24* | (2006.01) | |
| *B05C 17/01* | (2006.01) | |

(52) U.S. Cl.
CPC .. *A61B 17/12186* (2013.01); *A61B 17/12109* (2013.01); *A61M 5/31581* (2013.01); *A61M 5/3153* (2013.01); *A61M 2005/2411* (2013.01); *A61M 2005/31508* (2013.01); *B05C 17/0126* (2013.01)

(58) Field of Classification Search
CPC ............ A61M 5/31581; A61M 5/3153; A61M 5/31501; A61M 2005/2477; A61B 17/12186
See application file for complete search history.

(56) References Cited

U.S. PATENT DOCUMENTS

| 4,090,639 | A | * | 5/1978 | Campbell | ........... B05C 17/0123 |
| | | | | | 222/309 |
| 4,368,731 | A | * | 1/1983 | Schramm | .......... A61M 5/31595 |
| | | | | | 604/231 |
| 4,758,226 | A | | 7/1988 | Carre | |
| 5,236,105 | A | | 8/1993 | Galex | |

(Continued)

FOREIGN PATENT DOCUMENTS

| FR | 2526070 A1 | 11/1983 |
| WO | WO1999017833 | 4/1999 |
| WO | 2009154871 A1 | 12/2009 |

OTHER PUBLICATIONS

Extended European Search Report from counterpart European Patent Application No. 18166283.4, dated Sep. 25, 2018, 6 pp.

*Primary Examiner* — Nathan R Price
*Assistant Examiner* — Melissa A Snyder

(57) ABSTRACT

In some examples, a medical dispensing device includes a housing and a trigger. A first engager of the device is configured to move axially as the trigger pivots. As the first engager moves, it engages a rod. A maximum proximal position of the rod is defined by a stop. A spring presses the first engager into the trigger such that either the trigger or the first engager rests against a stop limiting rotation of the trigger. A second engager moves axially as the trigger pivots. At the actuated position the second engager, defined by a stop, the second engager limits proximal movement of the rod. An assembly transfers movement of the trigger to the second engager after the trigger has pivoted a threshold amount. A member of the assembly distally moves the second engager. Until it is at the actuated position, the second engager enables the rod to proximally move.

21 Claims, 13 Drawing Sheets

(56) References Cited

U.S. PATENT DOCUMENTS

| | | |
|---|---|---|
| 5,381,931 A | 1/1995 | Chang |
| 5,615,807 A | 4/1997 | Peng |
| 5,638,997 A | 6/1997 | Hawkins et al. |
| 5,755,362 A | 5/1998 | Rodriguez et al. |
| 5,759,171 A | 6/1998 | Coelho et al. |
| 5,779,155 A | 7/1998 | Schennum et al. |
| 5,893,488 A | 4/1999 | Hoag et al. |
| 6,691,899 B2 * | 2/2004 | Sung ................. B05C 17/01 222/391 |
| 7,946,453 B2 | 5/2011 | Voegele et al. |
| 7,959,612 B2 | 6/2011 | Thompson et al. |
| 8,235,256 B2 | 8/2012 | Green et al. |
| 2004/0210183 A1 * | 10/2004 | Schulz ................ A61M 5/3129 604/20 |
| 2015/0209821 A1 | 7/2015 | Pfahnl et al. |
| 2015/0250463 A1 | 9/2015 | Jamiolkowski et al. |

\* cited by examiner

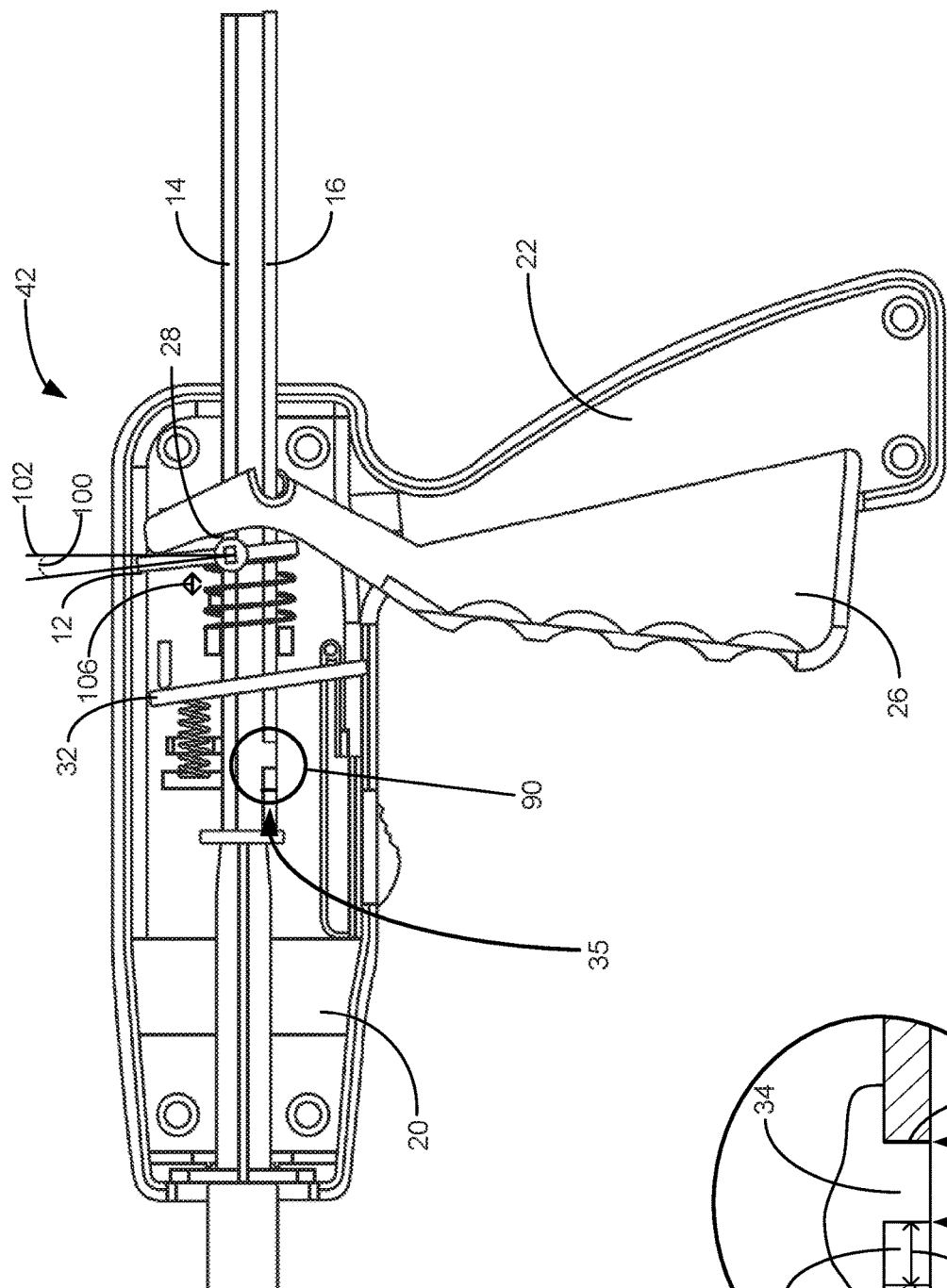
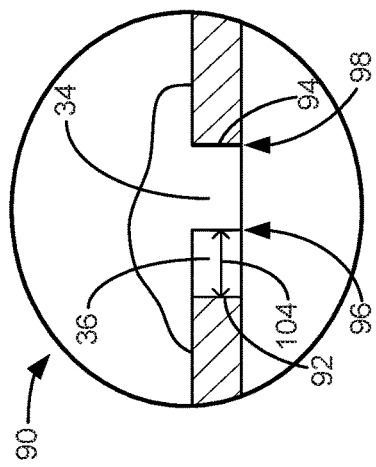
FIG. 3A
FIG. 3B

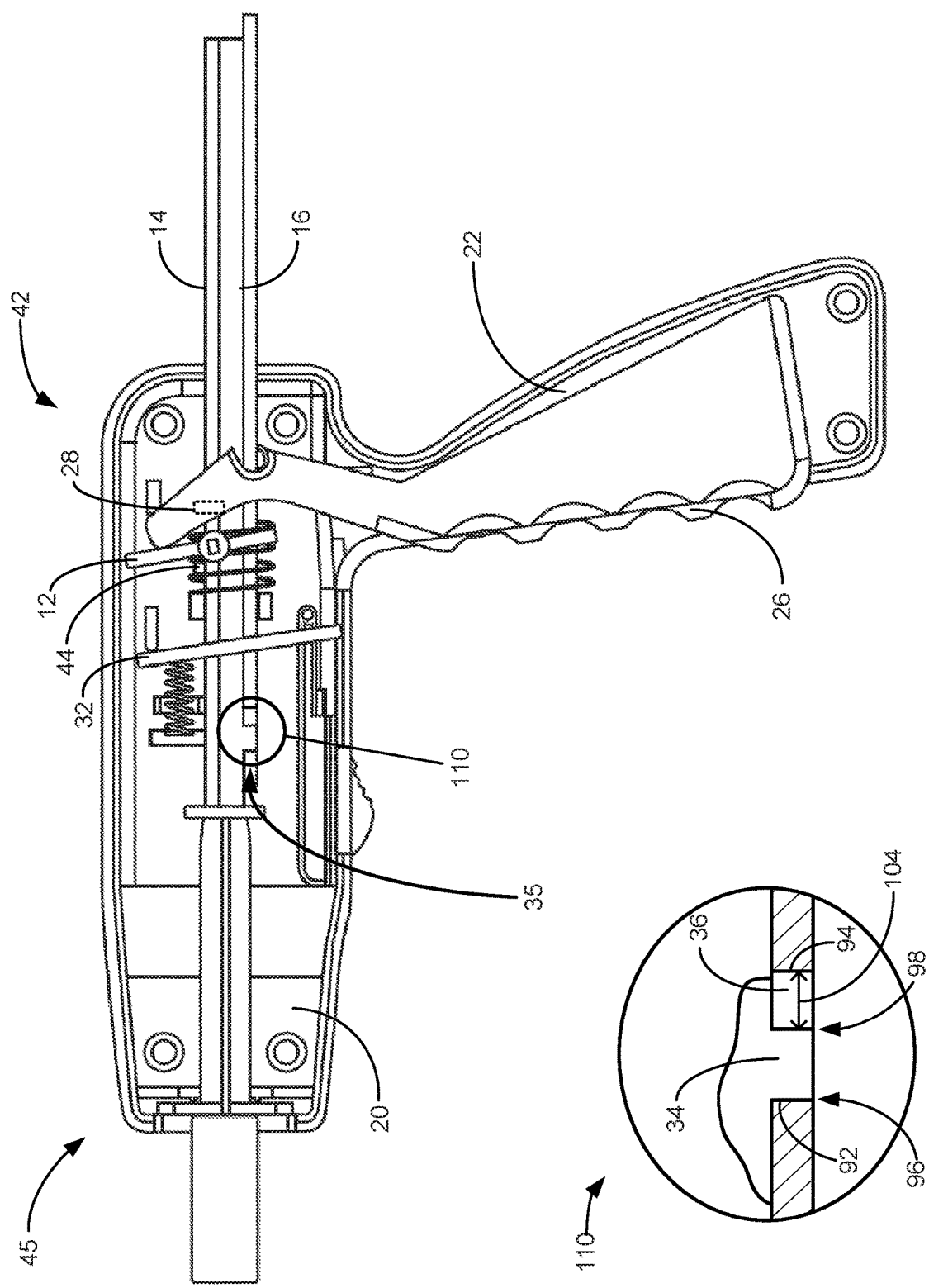

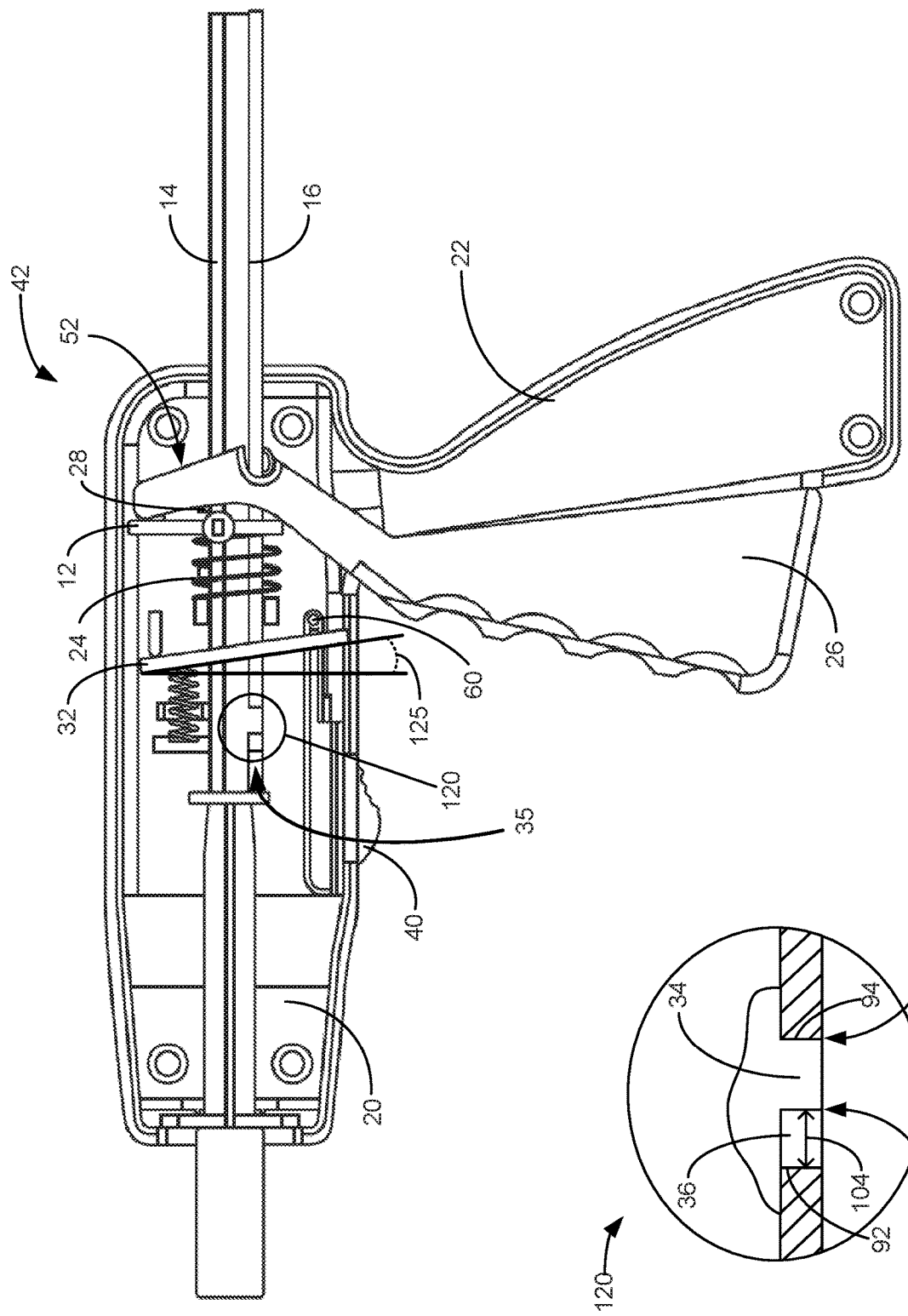

MEDICAL DISPENSING DEVICE

TECHNICAL FIELD

This disclosure relates to medical dispensing devices.

BACKGROUND

Some medical treatments include the application of viscous liquids. Viscous liquids can be used in a number of medical applications, such as the injection of a viscous vein occluding substance into a vein of a patient to close the vein, for example, to treat venous reflux. The occluding substance can be injected into a vein through a catheter.

Some dispensing devices that have been developed to deliver these viscous liquids have a handheld housing configured to hold a syringe containing the viscous liquid, and a trigger for actuating the syringe. Actuating the syringe may act to transport the viscous liquid into a catheter.

SUMMARY

In some aspects, this disclosure describes a medical dispensing device for dispensing materials, such as a medical adhesive. The medical dispensing device may be configured to actuate a rod towards a material reservoir a first predetermined amount with a single full pull of a trigger. Actuating the rod towards the material reservoir a first predetermined amount may result in the medical dispensing device delivering a predetermined aliquot (e.g., volume) of material from the material reservoir. For example, the movement of the rod towards the material reservoir may cause the material to be pushed out of the material reservoir. The medical dispensing device may be configured to initially actuate a rod towards a material reservoir more than is needed to dispense a desired aliquot, after which the rod may be retracted. This movement of the rod (moving towards the material a certain amount followed by retraction of the rod to the proper position, rather than simply immediately moving the rod to the proper position) may result in a high-pressure gradient, which enables the material to flow out of the material reservoir and, if a catheter is attached to the material reservoir, out of the catheter more quickly. That is, the material may be overpressurized by the rod, such that the material is delivered relatively quickly. Further, overpressurizing helps to ensure that the full, proper amount of the material is dispensed. The medical dispensing device may include a release button that is configured to reduce or substantially eliminate forces upon components of the medical dispensing device to enable these components to be returned to an initial state, such that the procedure can be repeated with substantially similar results.

In a first example, aspects of the disclosure relate to a medical dispensing device that includes: a frame comprising a housing and a handle that extends from a proximal portion of the housing; a rod positioned within the housing of the frame; a trigger affixed to the frame and configured to move relative to the handle; a first engager distal to a first portion of the trigger, wherein the first engager is configured to move distally when the trigger moves axially toward the handle and move proximally when the trigger moves axially away from the handle, wherein the first engager is configured to engage the rod as the first engager moves axially relative to the housing such that the rod undergoes a distal force when the first engager moves distally and the rod undergoes a proximal force when the first engager moves proximally; a distal hard stop limiting axial rotation of the trigger towards the handle, wherein a maximum distal position of the rod is defined by the distal hard stop; a compression spring that is engaged with the first engager; a proximal hard stop limiting axial rotation of the trigger away from the handle, wherein the compression spring presses the first engager into the trigger such that at least one of the trigger or the first engager is configured to rest against the proximal hard stop when the trigger is not actuated; a second engager that is configured to move axially relative to the housing, wherein the second engager limits proximal movement of the rod when the second engager is in contact with the rod at the actuated position; a second engager hard stop that defines an actuated position of the second engager relative to the housing; a movement transfer assembly configured to transfer movement of the trigger to the second engager such that the second engager moves distally when the trigger has moved axially towards the handle more than a threshold amount, wherein the movement transfer assembly includes a transferring member that distally moves the second engager relative to the housing as the trigger moves axially towards the handle after the trigger has moved axially towards the handle more than the threshold amount, wherein the second engager is configured to enable the rod to proximally move until the rod is in contact with the second engager while the second engager is at the actuated position.

In a second example relating to the medical dispensing device of the first example, the second engager is configured to be in a first position and the rod is configured to be in a second position when the at least one of the trigger or the first engager is resting against the proximal hard stop before the trigger has moved axially towards the handle more than the threshold amount, the medical dispensing device further including a release button that is configured to substantially eliminate forces that retain the second engager in a position other than the first position and retain the rod in a position other than the second position, enabling both the second engager to return to the first position and the rod to return to the second position.

In a third example relating to the medical dispensing device of the first example and/or the second example, the second engager is configured to disengage from the rod when the transferring member distally moves the second engager such that the rod is not in contact with the second engager.

In a fourth example relating to the medical dispensing device of the third example, the second engager is configured to engage the rod in response to the second engager moving proximally following the distal movement of the second engager by the transferring member.

In a fifth example relating to the medical dispensing device of any of the first through fourth examples, the trigger is configured to move into contact with the distal hard stop in response to a predetermined force exerted upon the trigger, the trigger being in contact with the distal hard stop resulting in a predetermined amount of distal rod actuation.

In a sixth example relating to the medical dispensing device of the fifth example, the compression spring is configured to force at least one of the trigger or the first engager to move into contact with the proximal hard stop in response to a termination of the predetermined force upon the trigger, and wherein the second engager is configured to move to the actuated position and the rod is configured to a move a predetermined amount in response to a termination of the predetermined force upon the trigger.

In a seventh example relating to the medical dispensing device of any of the first through sixth examples, a first position of the distal hard stop provides a first maximum distal position of the rod and a second position of the distal hard stop provides a second maximum distal position of the rod.

In an eighth example relating to the medical dispensing device of any of the first through seventh examples, the medical dispensing device further includes a retaining member that engages the second engager such that the second engager only axially moves towards a distal portion of the housing.

In a ninth example relating to the medical dispensing device of the eighth example, the transferring member is a tab of a first length extending radially out from the rod and the movement transfer assembly defines a slot of a second length of the second engager configured to receive the tab, the slot configured such that when the tab is received in the slot, a proximal surface of the tab is engaged with a proximal surface of the slot when the at least one of the trigger or the first engager is resting against the proximal hard stop before the trigger moves axially towards the handle more than the threshold amount, wherein a difference of the second length and the first length is substantially similar to the threshold amount such that the trigger rotating axially towards the handle the threshold amount results in a distal surface of the tab engaging a distal surface of the slot such that the proximal surface of the tab no longer engages the proximal surface of the slot, wherein the tab is configured to distally move the second engager as the rod distally moves when the distal surface of the tab is engaged with the distal surface of the slot.

In a tenth example relating to the medical dispensing device of the ninth example, the medical dispensing device is configured to modify the actuated position of the second engager by being configured to operate another second engager that has another slot of a third length, wherein the third length is different than the second length.

In an eleventh example relating to the medical dispensing device of any of the first through seventh examples, the compression spring includes a first compression spring and the movement transfer assembly further includes a second compression spring engaged with the second engager and configured to press into the second engager to engage the second engager with the second engager hard stop when the second engager is not actuated, wherein the transferring member protrudes proximally into the housing and is configured to move through the housing as the first engager moves axially through the housing, wherein the transferring member does not engage the second engager when the trigger rests against the proximal hard stop, the transferring member being configured to actuate the second engager when the transferring member is moved distally into the housing after the trigger has moved axially towards the handle more than the threshold amount, wherein the transferring member is configured to actuate the second engager by at least exerting a distal force upon the second engager, the distal force being sufficient to overcome the second compression spring holding the second engager against the second engager hard stop such that at least a portion of the second engager moves distally.

In a twelfth example relating to the medical dispensing device of any of the first through eleventh examples, the second engager is proximal to the handle, the trigger is proximal to the handle and is configured to move distally as the trigger moves axially towards the handle and to move proximally as the trigger moves axially away from the handle, and the movement transfer assembly includes: the transferring member extending proximally from the trigger; an absorbing member that extends distally from the second engager, wherein the absorbing member includes a flange on a distal edge of the absorbing member; and a plate affixed to the transferring member and coupling the transferring member to the absorbing member, wherein the plate defining an opening through which the absorbing member extends, the flange of the absorbing member being larger than the opening, wherein the plate is configured to slide over the absorbing member until the trigger has moved axially towards the handle at least the threshold amount, and to engage the flange upon the trigger rotating axially towards the handle at least the threshold amount such that the distal movement of the transferring member is transferred to both the absorbing member and the second engager.

In a thirteenth example relating to the medical dispensing device of any of the first through twelfth examples, the trigger is configured to pivot relative to the handle.

In a fourteenth example, aspects of the disclosure relate to a method of dispensing a medical substance includes actuating a rod distally a first distance to a maximum distal position using a first engager by applying a force upon a trigger of the medical dispensing device, the medical dispensing device including: a frame comprising a housing and a handle that extends from a proximal portion of the housing; a rod positioned within the housing of the frame; the trigger affixed to the frame and configured to move relative to the handle; the first engager distal to a first portion of the trigger, wherein the first engager moves distally when the trigger moves axially toward the handle and the first engager is configured to move distally when the trigger moves axially toward the handle and move proximally when the trigger moves axially away from the handle, wherein the first engager is configured to engage the rod as the first engager moves axially relative to the housing such that the rod undergoes a distal force when the first engager moves distally and the rod undergoes a proximal force when the first engager moves proximally; a distal hard stop limiting axial rotation of the trigger towards the handle, wherein the maximum distal position of the rod is defined by the distal hard stop; a compression spring that is engaged with the first engager; a proximal hard stop limiting axial rotation of the trigger away from the handle, wherein the compression spring presses the first engager into the trigger such that at least one of the trigger or the first engager is configured to rest against the proximal hard stop when the trigger is not actuated; a second engager that is configured to move axially relative to the housing, wherein the second engager limits proximal movement of the rod when the second engager is in contact with the rod at the actuated position; a second engager hard stop that defines an actuated position of the second engager relative to the housing; and a movement transfer assembly configured to transfer movement of the trigger to the second engager such that the second engager is configured to move distally when the trigger has moved axially towards the handle more than a threshold amount, wherein the movement transfer assembly includes a transferring member that distally moves the second engager relative to the housing as the trigger moves axially towards the handle after the trigger has moved axially towards the handle more than the threshold amount, wherein the second engager is configured to enable the rod to proximally move until the rod is in contact with the second engager while the second engager is at the actuated position; wherein the method further includes reducing a force upon the trigger such that at least one of a trigger or a first engager rests against the proximal hard stop, wherein reducing the force upon the trigger results in the rod proximally moving a second distance, wherein the second distance is less than the first distance.

In a fifteenth example relating to the method of the fourteenth example, the method further includes modifying the maximum distal position of the rod by replacing the distal hard stop with another distal hard stop, where the distal hard stop has a first width and the another distal hard stop has a second width.

In a sixteenth example relating to the method of any of the fourteenth through fifteenth examples, the transferring member is a tab of a first length extending radially out from the rod, wherein the movement transfer assembly defines a slot of a second length of the second engager configured to receive the tab, the slot configured such when the tab is received in the slot, a proximal surface of the tab is engaged with a proximal surface of the slot when the at least one of the trigger or the first engager is resting against the proximal hard stop before the trigger moves axially towards the handle more than the threshold amount, wherein a difference of the second length and the first length is substantially similar to the threshold amount such that the trigger rotating axially towards the handle the threshold amount results in a distal surface of the tab engaging a distal surface of the slot such that the proximal surface of the tab no longer engages the proximal surface of the slot, wherein the tab is configured to distally move the second engager as the rod distally moves when the distal surface of the tab is engaged with the distal surface of the slot.

In a seventeenth example relating to the method of the sixteenth example, the method further includes modifying the actuated position of the second engager by replacing the second engager with another second engager that has another slot of a third length, wherein the third length is different than the second length.

In an eighteenth example relating to the method of any of the fourteenth through fifteenth examples, the compression spring comprises a first compression spring, wherein the movement transfer assembly includes a second compression spring that is engaged with the second engager and configured to press into the second engager to engage the second engager with the second engager hard stop when the second engager is not actuated, wherein the transferring member protrudes proximally into the housing and is configured to move through the housing as the first engager moves axially through the housing, wherein the transferring member does not engage the second engager when the trigger rests against the proximal hard stop and moves axially through the housing as the first engager moves axially through the housing, the transferring member being configured to actuate the second engager when the transferring member is moved distally into the housing after the trigger has moved axially towards the handle more than the threshold amount, wherein the transferring member is configured to actuate the second engager by at least exerting a distal force upon the second engager, the distal force being sufficient to overcome the second compression spring holding the second engager against the second engager hard stop such that at least a portion of the second engager moves distally.

In a nineteenth example relating to the method of any of the fourteenth through fifteenth examples, the second engager is proximal to the handle, the trigger is proximal to the handle and is configured to move distally as the trigger moves axially towards the handle and to move proximally as the trigger moves axially away from the handle, and the movement transfer assembly includes: the transferring member extending proximally from the trigger; an absorbing member that extends distally from the second engager, wherein the absorbing member includes a flange on a distal edge of the absorbing member; and a plate affixed to the transferring member and coupling the transferring member to the absorbing member, wherein the plate defining an opening through which the absorbing member extends, the flange of the absorbing member being larger than the opening, wherein the plate is configured to slide over the absorbing member until the trigger has moved axially towards the handle at least the threshold amount, and to engage the flange upon the trigger rotating axially towards the handle at least the threshold amount such that the distal movement of the transferring member is transferred to both the absorbing member and the second engager.

In a twentieth example, aspects of the disclosure relate to a medical dispensing device for dispensing materials by actuating a rod distally toward a material reservoir, the medical dispensing device including: a frame comprising a housing that houses the rod and a handle that extends from a proximal portion of the housing; a trigger affixed to the frame and configured to pivot axially about a pivot point towards and away from the handle; a first engager that is configured immediately distal to a first portion of the trigger, wherein the first engager moves distally when the trigger pivots axially toward the handle and the first engager moves proximally when the trigger pivots axially away from the handle, wherein the first engager is configured to engage the rod as the first engager moves axially relative to the housing such that the rod undergoes a distal force when the first engager moves distally and the rod undergoes a proximal force when the first engager moves proximally; a second engager that is configured to move axially relative to the housing, wherein the second engager limits proximal movement of the rod when the second engager is in contact with the rod at an actuated position of the second engager; and means for absorbing and transferring movement of the trigger onto the second engager such that the second engager only moves if the trigger has pivoted axially towards the handle more than a threshold amount, wherein the means for absorbing and transferring movement of the trigger onto the second engager distally moves the second engager along the housing as the trigger pivots axially towards the handle after the trigger has pivoted axially towards the handle more than a threshold amount, wherein the means for absorbing and transferring movement of the trigger onto the second engager defines both a maximum distal position of the rod and the actuated position of the second engager.

In a twenty-first example relating to the medical dispensing device of the twentieth example, means for absorbing and transferring movement of the trigger onto the second engager results in overpressurization of forces upon the rod as the rod axially moves to the maximum distal position.

The details of one or more examples are set forth in the accompanying drawings and the description below. Other features, objects, and advantages will be apparent from the description and drawings, and from the claims.

BRIEF DESCRIPTION OF THE DRAWINGS

FIGS. 3A-3B depict a cross sectional view and detail view, respectively, of a partially-actuated example medical dispensing device.

FIGS. 4A-4B depict a cross sectional view and detail view, respectively, of a fully-actuated example medical dispensing device.

FIGS. 5A-5B depict a cross sectional view and detail view, respectively, of an example medical dispensing device after it has been fully actuated and released.

DETAILED DESCRIPTION

Figure 1:
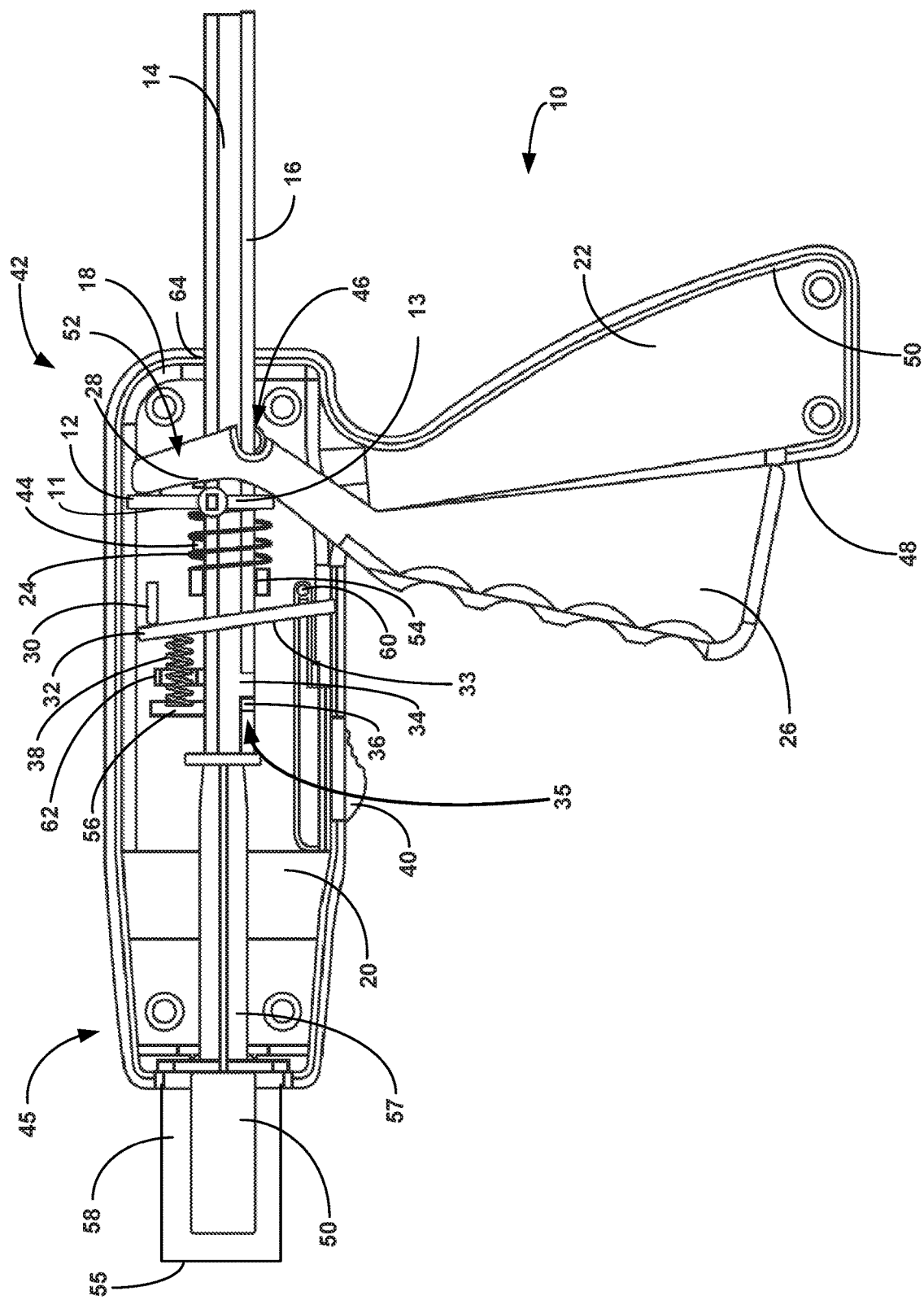
FIG. 1 depicts a cross-sectional view of an example medical dispensing device.

Medical dispensing devices may need to dispense a material out through a catheter attached to a distal portion of the medical dispensing device. In certain cases, the catheter may be relatively long and narrow, and the material may be particularly viscous. As a result, some medical dispensing devices may have difficulty applying a sufficient amount of pressure upon a material reservoir to dispense a sufficient aliquot (e.g., amount) of material out a distal end of an attached catheter. In certain instances, a medical dispensing device may apply near to 100% of a pressure needed to dispense a viscous material out of a relatively long catheter, but due to the viscous nature of the material it may take a relatively long time (e.g., thirty seconds or a minute, depending on a length of the catheter) for the material to travel the distance of the catheter to be dispensed.

Example medical dispensing devices are described herein that include a housing configured to mechanically connect to a syringe containing a viscous substance (e.g., a medical adhesive), and a trigger and a rod that actuates the syringe (or other material reservoir). Pulling the trigger to actuate the device may cause corresponding movement of the rod towards the syringe, and the rod may engage with the syringe (directly or indirectly) to cause a medical substance within the syringe to be expelled from a distal end of the syringe. Devices described herein are configured to reliably dispense predetermined aliquots in response to predefined user actions (e.g., a full press and release of a trigger of a device).

In some examples, the medical dispensing device may be configured to overpressurize the material reservoir of the syringe. A medical dispensing device may be configured to overpressurize the material reservoir by moving a rod into a syringe a relatively larger distance than the distance required to dispense the appropriate amount of the substance out of the distal end of the syringe or the distal end of a catheter fluidically connected to the syringe. By overpressurizing the material reservoir, the medical dispensing device may reliably dispense the viscous substance in a timely manner, which may be less than the same amount of time required to dispense the material from the same syringe without overpressurization. For example, if a rod needs to move distally 1 centimeter (cm) to dispense the desired aliquot of material, the medical dispensing device may be configured to move the rod distally 4 centimeters.

Further, the medical dispensing device may be configured to release an amount of pressure equal to the overpressurization of the material reservoir of the syringe. For example, the medical dispensing device may be configured to release this pressure by retracting the rod from the material reservoir a certain amount. Continuing the example above, after moving the rod distally (towards the material reservoir) 4 centimeters, the rod may be configured to move proximally (away from the material reservoir) 3 centimeters. By initially overpressurizing until the substance is dispensed, followed by releasing pressure until the rod moves a certain net distance, the medical dispensing device may be configured to quickly apply the desired aliquot and then prevent any extra substance from being dispensed such that only the intended aliquot is dispensed.

Towards this end, it may be desirable to limit proximal movement of a rod of the medical dispensing device after a trigger is pulled. For example, preventing the rod from moving back to an initial position (prior to pulling the trigger) may result in dispensing benefits, as a medical dispensing device may avoid unintentionally creating a pseudo-vacuum that retracts injected viscous liquid back into a syringe.

In certain examples, a medical dispensing device may include a toothed structure to hold a rod in place after a trigger is pulled. However, in this configuration, with the teeth engaging the rod, it may be difficult to release pressure within the medical dispensing device. Further, in instances where it is desired to axially move the rod back and forth, it may be difficult or impossible to do so with the teeth engaging the rod, as the force between the teeth and rod may need to be overcome in order to move the rod further proximally. Also, in instances where it is desired to reset the entirety of the dispensing device back to an original position (e.g., prior to any trigger pulls or the position when a syringe containing the medical substance was first introduced into the handle of the dispensing device), it may be difficult or impossible as the teeth are engaging the rod and associated components.

Further, a medical dispensing device that uses teeth to hold a rod (configured to engage a syringe to dispense material from the syringe) may have the singular capacity to actuate only one syringe size (e.g., a 3 cubic centimeter (cc) syringe). While this one syringe size may work well for some medical applications using viscous liquids, the lack of ability to interchange syringes may impair the ability of the example medical dispensing device to perform other medical applications. Additionally, it may be difficult or expensive to manufacture teeth that are small enough to dispense relatively small aliquots, and/or are small enough to precisely dispense numerous aliquots that are all within a relatively small range. Further, such small teeth would may be relatively fragile and prone to manufacturing defects and/or incidental breakage in response to potentially nominal forces.

Aspects of the disclosure relate to a medical dispensing device that has a rod, a trigger, a first engager, and a second engager. The medical dispensing device may dispense a viscous liquid (e.g., a medical adhesive). The first engager may engage with the rod when the trigger is pulled. Actuating the trigger may distally move the rod with the first engager. Releasing the trigger may result in the first engager moving proximally. The rod may be a smooth rod (e.g., a rod that does not have teeth). Nonetheless, despite the lack of teeth, in some examples the second engager is configured to prevent the rod from moving proximally more than a threshold amount after the rod has moved distally at least a threshold amount. Enabling a smooth rod to move proximally a threshold amount after the rod has moved distally a threshold amount may enable a better application of the viscous liquid. For example, as discussed above, retracting the rod a relatively small amount after advancing the rod a relatively large amount, where the difference between the large and small amounts equates to the required distance to dispense the desired aliquot, may result in a relatively quick dispensing of the desired aliquot of material.

Also, in some examples the medical dispensing device may include a release button. The release button may reduce or substantially eliminate forces upon components of the medical dispensing device such that the rod is exerting no pressure on a material reservoir. Enabling the reduction or elimination of forces upon components of the medical dispensing device may improve the ability of a medical dispensing device to repeatedly apply a viscous liquid. Further, the medical dispensing device may be configured to receive (or otherwise connect to) a plurality of syringe sizes (e.g., a 3 cc syringe size, as well as larger syringe sizes) while maintaining/improving the predictability of how quick and far the rod may move in the medical dispensing device, which may equate to flow rate and dispense volume of a dispensed material. Being configured to accommodate larger syringe sizes may provide more versatility for such a medical dispensing device. For example, accommodating larger syringe sizes may enable the medical dispensing device to treat relatively longer veins, treat relatively wider veins (e.g., veins with a relatively larger diameter), be operated with relatively fewer steps over a relatively shorter amount of time, and/or reduce recanalization of vein segments.

FIG. 1 depicts a cross-sectional view of an example medical dispensing device 10. The medical dispensing device 10 has a proximal portion 42 and a distal portion 45, and includes a first engager 12, a rod 14, a second engager 16, a frame 18, a first compression spring 24, a trigger 26, a second compression spring 38, and a release button 40. A distal end of the frame 18 is configured to mechanically connect to a materials reservoir 58, which may be, for example, a syringe. The materials reservoir 58 may be configured to fluidically connect to a medical device, such as a catheter, which may be used to deliver the material stored by the reservoir 58 to a patient. The medical dispensing device 10 may be configured to dispense a material from a distal opening 55 at the distal end of the material reservoir 58 by actuating the rod 14 distally towards the material reservoir 58. The rod 14 is configured to engage with a proximal portion of the material reservoir 58 (e.g., via a syringe plunger 57), which causes the pressure within the material reservoir 58 to increase, thereby causing the material to dispense out of the distal opening 55 of the material reservoir 58. In some examples, the material that is dispensed from the material reservoir 58 may include a viscous liquid. For example, the medical dispensing device 10 may be configured to dispense a medical adhesive, such as a medical adhesive dispensed into a vein of a patient in order to close the vein. In other examples, the medical dispensing device 10 may be configured to dispense sclerosant agents, tPA, etc.

In some examples, the rod 14 may be a machined piece of metal in order to ensure that proper tolerances are met (e.g., to ensure that a predetermined axial movement of the first engager 12 results in a predetermined axial force upon the rod 14). However, in other examples, the rod 14 may be formed from or otherwise include another suitable material (e.g., a polymer) or using another suitable technique (e.g., molding).

In the example shown in FIG. 1, a distal end of the rod 14 is configured to engage with (e.g., directly or indirectly via an intermediate component) a proximal end of the material reservoir 58, such as through a syringe plunger 57. Thus, moving the rod 14 distally causes rod 14 to apply a pushing force to the proximal end of the material reservoir 58, which may result in material being dispensed from the distal end of the material reservoir 58. The configuration of the medical dispensing device 10 that causes the rod 14 to be pushed distally in response to user actuation of the trigger 26 is described in further detail below.

The frame 18 may be constructed out of any suitable material. In some examples, the frame 18 is a single unitary plastic component that is manufactured using injection molding. In other examples, the frame 18 is made of a different material, includes numerous subsections (e.g., rather than being a single unitary structure), and/or is constructed using a different process. It is to be understood that the relative lengths and angles of the depicted frame 18, as well as the relative lengths and angles of the other components of the medical dispensing device 10, are for purposes of illustration only; other relative lengths and angles that are consistent with aspects of the disclosure are contemplated and possible.

The frame 18 may include a housing 20 configured to house the rod 14 and a handle 22 that extends from a proximal portion 42 of the frame 18. The trigger 26 may be affixed to the frame 18 and be configured to move relative to the handle 22 in order to move the rod 14 distally relative to the frame 18. The frame 18 and housing 20 may be integral (i.e., a unitary component, as shown), or the frame 18 and housing 20 may be separate components, with the housing 20 configured to engage around the frame 18. In the example shown in FIG. 1, the trigger 26 is configured to pivot axially around a pivot point 46 towards and away from the handle 22. In other examples, the trigger 26 may be configured for another movement relative to the handle 22, such as a linear movement towards and away from the handle 22. Thus, although pivoting of the trigger 26 relative to the handle 22 is primarily referred to herein, in other examples, at least a portion of the trigger 26 may move relative to the handle 22 in other motions and/or directions.

The trigger 26 may be formed from any suitable material, and may include the same material as the frame 18 or a different material. For example, the trigger 26 may be a plastic injection-molded component. In some examples, a distal portion of the trigger 26 may be treated or coated with a material to make the trigger 26 easier or softer to grip. In certain examples, the handle 22 and a distal portion of the trigger 26 may be ergonomically shaped to fit the hand of an operator (e.g., the trigger 26 may be shaped with finger grooves as depicted).

In some examples, the handle 22 may be partially hollow and define a slot in the distal wall 48 configured to receive at least part of the trigger 26, such that the trigger 26 may be configured to pivot at least partially into the handle 22. In such examples, some portion of a proximal wall 50 of the handle 22 may be configured to act as a hard stop to block proximal motion of the trigger 26 past the portion of the proximal wall 50. In other examples, the handle 22 and the trigger 26 may be configured such that some or all of the distal wall 48 blocks rotation into the handle 22, such that the trigger 26 is not able to pivot much or at all into the handle 22. In such examples, some portion of the distal wall 48 may be configured to act as a hard stop that blocks proximal movement of the trigger 26.

The trigger 26 may be affixed to the frame 18 using any suitable technique. For example, the trigger 26 may be pinned at a single point to the frame 18, such that the trigger 26 can pivot around the pin(s). In some examples, the trigger 26 may have flanges that rotate around rods as discussed in greater detail in FIG. 2.

The first engager 12 may be composed of any suitable material that is rigid enough to provide the functions attributed to the first engager 12 in this disclosure. For example, the first engager 12 may be formed of a polymer or a metal. In some examples, the first engager 12 may be a machined (e.g., constructed using a computer-numeric control (CNC) device) portion of a metal plate.

The first engager 12 is positioned within the dispensing device 10 at a location immediately distal to a first portion 52 of the trigger 26. The first portion 52 of the trigger 26 may be located near or within the housing 20 of the frame 18, as depicted in FIG. 1. The first engager 12 may be configured to move distally when the trigger 26 pivots axially toward or into the handle 22 as discussed herein. In some examples, the first portion 52 of the trigger 26 may physically push the first engager 12 distally as the trigger 26 pivots axially toward or into the handle 22. Further, the first engager 12 may be configured to move proximally when the trigger 26 pivots axially away from the handle 22. In some examples, a first compression spring 24 may press the first engager 12 against the first portion 52 of the trigger 26, such that the first engager 12 moves proximally as the trigger 26 pivots axially away from the handle 22.

In some examples, the first engager 12 is affixed to the housing 20 or the trigger 26, and is substantially fixed in place relative to the housing 20 or the trigger 26. In other examples, the first engager 12 is configured to "float" within the frame 18 between the trigger 26 and the first compression spring 24, such that it is housed within the housing 20 but may move relative to the housing 20, the trigger 26, or both the housing 20 and the trigger 26.

As noted above, the first compression spring 24 is configured to urge the first engager 12 into contact with the trigger 26. The first compression spring 24 may be any suitable spring element, such as, but not limited to, a metal spring. In some examples, the first compression spring 24 may be configured to always be in contact with the first engager 12. For example, the first compression spring 24 may be configured to press into a distal surface 11 of the first engager 12. Because the first compression spring 24 is configured to press into the distal surface 11 of the first engager 12, the initial position of the medical dispensing device 10 (e.g., the relative alignment of the components of the medical dispensing device 10 when an operator is not actuating or exerting a force upon the trigger 26 or any other part of the medical dispensing device 10) may include the trigger 26 pivoted away from the handle 22 and the first engager 12 in a proximal-most position as depicted in FIG. 1.

In some examples, the first compression spring 24 may be configured to contact a portion 13 of the distal surface 11 of the first engager 12 that is closer to the handle 22 (e.g., rather than the first compression spring 24 being configured to contact the center of the distal surface 11). The first compression spring 24 be configured to press the portion 13 of the distal surface 11 of the first engager 12 into the trigger 26. The first compression spring 24 contacting the portion 13 of the first engager 12 along with the profile of the trigger 26 (e.g., the profile as seen in FIG. 1) may cause the portion 13 of the first engager 12 to angle back towards the proximal portion 42 of the housing 20 as the trigger 26 is actuated as described herein, such that the first engager 12 engages the rod 14 as the trigger 26 is actuated.

In some examples, the first compression spring 24 is not fixed in place relative to the frame 18, but, rather, may be configured to "float" within the frame 18 between the first engager 12 and a support 54 for the first compression spring 24. The support 54 for the first compression spring 24 is shown in greater detail in FIG. 2. In some examples, the first compression spring 24 may be configured to wind around the rod 14, such that the rod 14 travels axially through the first compression spring 24. A minimal predetermined amount of force may be sufficient to overpower the force of the first compression spring 24 (e.g., the spring force of the first compression spring, as determined by Hooke's law) while holding the first engager 12 in contact with the trigger 26 such that the trigger 26 can be actuated. For example, the force sufficient to overpower the force of the first compression spring 24 may be between an amount that is relatively easy for a user to provide while operating the medical dispensing device 10.

The first engager 12 may be configured to engage the rod 14 as the first engager 12 moves axially through the housing 20. The axial direction can be, for example, along a longitudinal axis of the rod 14. The first engager 12 may engage the rod 14 such that the rod 14 undergoes a distal force (e.g., a force acting upon the rod 14 towards the distal portion 45 of the housing 20) when the first engager 12 moves distally and a proximal force (e.g., a force acting upon the rod 14 towards the proximal portion 42 of the housing 20) when the first engager 12 moves proximally. The interaction of the first engager 12 and the rod 14 is discussed in more detail in FIGS. 6A-6C. In some examples, the first engager 12 is not engaged with (e.g., is not in physical contact with) the rod 14 if the trigger 26 is not actuated as depicted in FIG. 1. Thus, in some examples, in the initial position of the first engager 12, the first engager 12 does not engage the rod 14. In other examples, however, in the initial position of the first engager 12, the first engager 12 may engage with the rod 14.

It may be useful in some cases to limit axial movement of the first engager 12. For example, a designer of the medical dispensing device 10 and/or an operator of the medical dispensing device 10 may know an exact amount of distal movement of the rod 14 that is required to dispense a desired aliquot of the material of the medical dispensing device 10. In this example, the designer or operator may configure the medical dispensing device 10 to limit the axial movement of the first engager 12 such that a single actuation of the medical dispensing device 10 (e.g., a single full pull of the trigger 26 towards the handle 22 and subsequent release of the trigger 26) actuates the rod 14 the exact amount, rather than a user of the medical dispensing device 10 having to estimate when the known exact amount of distal movement is achieved and controlling release of the trigger 26 at the time corresponding to such distal movement. Further, in some examples, if the first engager 12 is configured to distally move the rod 14 the exact amount upon a pull of the trigger 26, it may take a relatively long time for the material to travel through a catheter fluidically connected to a distal end of the material reservoir 58 to reach the intended destination. Therefore, the medical dispensing device 10 may be configured to only limit the movement of the first engager 12 after the first engager 12 has moved the rod 14 past the exact amount necessary to overpressurize the material and dispense the material relatively quicker, thereafter enabling the rod 14 to move proximally back until the rod 14 has a net movement that is equal to the exact amount necessary. As such, in some examples, the first engager 12 may be configured to overpressurize the material such that the material is dispensed from the medical dispensing device 10 at a relatively fast pace.

In the example shown in FIG. 1, the amount of axial movement of the first engager 12 is defined by a pair of hard stops 28, 44. The hard stops 28, 44 may be any suitable structure that physically stops the first engager 12 from moving in the axial direction. For example, one or both of the hard stops 28, 44 can be ridges that extend radially inward from the housing 20, as shown in FIG. 1. A proximal hard stop 28 may define a proximal-most position that the first engager 12 may move to, and a distal hard stop 44 may define a distal-most position that the first engager 12 may move to. The geometry and interaction of the first engager 12 and the pair of hard stops 28, 44 is discussed in greater detail below in relation to FIGS. 6A-6C. Being as the first engager 12 may be constantly engaged with the trigger 26, in some examples the pair of hard stops 28, 44 may be configured to define the limits to where the trigger 26 may pivot. For example, the trigger 26 may be configured to only pivot axially away from the handle 22 until the first engager 12 encounters the proximal hard stop 28, and the trigger 26 may be configured to only pivot axially into/toward the handle 22 until the first engager 12 encounters the distal hard stop 44. While FIG. 1, being a cross-sectional view, depicts a single proximal hard stop 28 and a single distal hard stop 44, it is to be understood that in some examples the housing 20 may include a pair of distal hard stops 44A, 44B and a pair of proximal hard stops 28A, 28B to extend in from both directions, as shown in greater detail in FIG. 6C.

In some examples, in the initial position of the trigger 26, the first engager 12 may be configured to be in contact with (and pressed against) the proximal hard stop 28. For example, the first compression spring 24 may be configured to press the first engager 12 against the proximal hard stop 28. As a result of the first engager 12 pressing against the proximal hard stop 28, the trigger 26 may be biased to be pivoted out away from the handle 22 to a distal-most position when the trigger 26 is in the initial position. An example manner in which the first engager 12 can be pressed against the proximal hard stop 28 is discussed more in FIGS. 6A-6C.

In some examples, the proximal hard stop 28 may be a formed part of the housing 20 (e.g., a feature formed during an injection-molding manufacturing process for the frame 18), such that the proximal hard stop 28 is a pseudo-permanent feature of the housing 20. However, in other examples, the proximal hard stop 28 may be formed separately from the housing 20 and mechanically connected to the housing 20 using any suitable technique, such as using an adhesive, welding, or an attachment mechanism (e.g., a screw, bolt, and the like).

In some examples, the distal hard stop 44 may be configured to be a separate piece that can be press fit into the housing 20. The fit between the housing 20 and the distal hard stop 44 may be configured to be tight enough that an operator may need to use special tools to insert and/or remove the distal hard stop 44. Alternatively, the fit between the housing 20 and the distal hard stop 44 may be configured to be loose enough that an operator may not need to use any special tools to insert and/or remove the distal hard stop 44 (e.g., a distal hard stop 44 may be inserted and/or removed from the housing 20 by hand). In certain examples, the housing 20 is configured to receive different distal hard stops 44. In such examples, the different hard stops 44 may have different dimensions, such that the first engager 12 may move to a different distal location depending on the particular distal hard stop 44 inserted in the housing 20. In this way, a user may modify the defined path of the first engager 12, which may enable the medical dispensing device 10 to apply different amounts of a viscous liquid depending upon the inserted distal hard stop 44. The user may thus customize the dispensing device 10 to accommodate different medical procedures.

For example, a user (e.g., clinician) may customize the medical dispensing device 10 to accommodate using the medical dispensing device 10 for different vessel sizes. In such examples, a different vessel size may require a different aliquot of material to adequately complete a medical procedure. As an example, a larger aliquot of material may be desirable for a larger vessel size, e.g., if the material is being used to occlude the vessel. A clinician may measure a vessel size of a patient, look up a proper aliquot for the measured vessel size in a chart or table or program, and then adjust the respective hard stops 44 such that medical dispensing device 10 may only dispense the proper aliquot in response to a trigger pull.

In the example shown in in FIG. 1, the device 10 includes a second engager 16 configured to engage the rod 14. The second engager 16 may be configured to limit the proximal movement of the rod 14 such that the rod 14 stops at a position that corresponds to the dispensation of the desired aliquot of the material. The second engager 16 engages the rod 16 using the movement transfer assembly 35. The movement transfer assembly 35 includes a slot 36 of the second engager 16 and a tab 34 of rod 14. The slot 36 may be the transferring member of the movement transfer assembly 35. The movement transfer assembly 35 is configured to transfer movement of the trigger 26 to the second engager 16. For example, once the trigger 26 has pivoted at least a threshold amount of distance into/toward the handle 22, the movement transfer assembly 35 moves the second engager 16 towards a distal portion 45 of the housing 20. As used herein, the threshold distance that the trigger 26 must pivot into the handle 22 may be a linear distance (e.g., rather than a rotation distance). Further, in some examples the threshold distance is from a distal surface of the trigger 26 relative to the handle 22.

For example, a desired aliquot may require the rod 14 moving two centimeters towards a distal portion 45 of the medical dispensing device 10. The first engager 12 may be configured to distally move the rod 14 three centimeters upon a full depression of the trigger 26, therein overpressurizing the material (e.g., putting more pressure on the material relative to if the rod 14 only moved two centimeters) to dispense the material relatively quickly (e.g., quicker than if the rod 14 only moved two centimeters). Upon the release of the trigger 26, the second engager 16 (along with the movement transfer assembly 35) may be configured to enable the rod 14 to move proximally one centimeters, after which the second engager 16 may be configured to engage the rod 14 and therein prevent the rod 14 from further proximal movement. In this way, the second engager 16 may be configured to ensure that the net movement of the rod 14 is the distance that equates to the proper aliquot (2 centimeters) when the trigger 26 is fully pressed and then released. As such, in some examples, the second engager 16 may be configured to ensure that the proper predetermined aliquot is dispensed upon a full actuation of the medical dispensing device 10.

The second engager 16 may be composed of metal, a polymer, or another suitable material or combinations thereof. In some examples, the second engager 16 may be a machined portion of a plate to ensure that predetermined tolerances of the second engager 16 are met, similar to the first engager 12. The second engager 16 may be configured to move axially relative to the housing 20 from an initial position. The initial position may include a location of the second engager 16 before the trigger 26 is actuated.

In some examples, both the second engager 16 and the rod 14 may be arranged in the frame 18 such that neither the second engager 16 nor the rod 14 may move either closer to the handle 22 or further away from the handle 22. Put differently, the second engager 16 and the rod 14 may be configured such that both are substantially immobilized such that neither may move in any direction other than axially along the length of the housing 20. A hole 64 in the proximal portion 42 of the housing 20 may be configured to limit or even prevent non-axial movement of the rod 14 and second engager 16. Further, a hole within the support 54 for the first compression spring 24 may be configured to block non-axial movement of the rod 14 and second engager 16.

A retaining member 32 may be configured to prevent the proximal movement of the second engager 16. In some examples, the retaining member 32 is always engaged with the second engager 16 (e.g., such that the retaining member 32 only disengages the second engager 16 when the release button 40 is actuated). In other examples, the retaining member 32 may be brought into engagement with the second engager 16, e.g., in response to actuation of the trigger 26. The retaining member 32 may be made of any suitable material, such as, but not limited to metal or a polymer. The retaining member 32 may be configured to be held in place by a second compression spring 38 and a second engager hard stop 30. In some examples, the retaining member 32 may be configured to only interface with the compression spring 38 and the hard stop 30 while not interfacing with the rod 14, as discussed in more detail in FIGS. 7A and 7B. In other examples, the retaining member 32 may also interface with a release button 40, such that the retaining member 32 is in contact with an arm 60 of the release button 40. The arm 60 may stabilize (e.g., hold in place) the retaining member 32. Further, in some examples, the retaining member 32 may be configured to axially move towards the distal portion 45 of the housing 20 in response to the release button 40 being pushed. In response to the release button 40 being pushed, the arm 60 of the release button 40 is configured to provide a distal force upon the retaining member 32 that axially moves the retaining member 32 in a distal direction.

The second compression spring 38 may be configured to press against a distal surface 33 of the retaining member 32. In other examples, the second compression spring 38 may press against different surfaces of the retaining member 32. In some examples, the second compression spring 38 is fixed relative to the housing 20. In other examples, such as the one shown in FIG. 1, however, the second compression spring 38 may be configured to "float" within the medical dispensing device 10, pressed between the retaining member 32 and a support 56 for the second compression spring 38. The second compression spring 38 may be made of metal, a polymer, or another suitable material. In some examples, the second compression spring 38 may have a second support 62 to prevent the second compression spring 38 from deflecting radially towards the housing 20.

The second engager 16, in conjunction with the retaining member 32, may be configured to limit the proximal movement of the rod 14 using a movement transfer assembly 35. For example, the second engager 16 may be configured to limit proximal movement of the rod 14 when the second engager 16 is in contact with the rod 14 and the second engager 16 is in an actuated position (discussed more in FIGS. 5A-5B).

As will be discussed more in FIGS. 3A-5B, a distal surface 96 of tab 34 is configured to contact a distal surface 92 of slot 36 to move the second engager 16 in a distal direction. In some examples, if the trigger 26 does not pivot at least the threshold amount into/toward the handle 22, then the second engager 16 will not axially move, even as the other components (e.g., trigger 26, first engager 12, rod 14) of the medical dispensing device 10 move axially in either distal or proximal directions. As such, being as the second engager 16 is still in the initial position (rather than the actuated position), the second engager 16 may be configured to not limit proximal movement of the rod 14 until the trigger 26 has moved at least the threshold amount as discussed herein.

After the trigger 26 has actuated the threshold amount, the second engager 16 may be configured to enable the rod 14 to proximally move until the rod 14 is in contact with the second engager 16 while the second engager 16 is in the actuated position. In some examples, the actuated position of the second engager 16 may be the position that the second engager 16 is in after the trigger 26 pivots at least the threshold amount and then pivots away from the handle 22. The second engager 16 may be configured to contact the rod 14 when a proximal surface 98 of the tab 34 contacts a proximal surface 94 of the slot 36.

In some examples, different versions of the second engager 16 have slots 36 of different dimensions. Altering the dimensions of the slot 36 may configure the rod 14 to axially move different lengths before the tab 34 of the rod 14 contacts either a distal or proximal surface of the slot 36. In some examples, the medical dispensing device 10 may be configured to be disassembled so that one version of the second engager 16 with a first set of slot 36 dimensions may be replaced with a second version of the second engager 16 that has a second set of slot 36 dimensions. Configuring the medical dispensing device 10 to operate with different varieties of second engager 16, therein configuring a defined path of the rod 14 to be altered, may enable the medical dispensing device 10 to apply different amounts of a material from the reservoir 58 depending upon the dimensions of the slot of the second engager 16.

In some examples, the medical dispensing device 10 may be configured to increase/decrease the amount the rod 14 moves in a proximal direction in response to increasing/decreasing the amount that the rod 14 moves in a distal direction, respectively. Configuring/operating the medical dispensing device 10 in this way may maintain a relatively constant rate of pressure-release following a full trigger 26 actuation (e.g., pressing the trigger 26 into the handle 22 followed by a full release of the trigger 26). In other examples, the enabled distal movement of the rod 14 may be altered independently, resulting in differing rates of release of pressure depending upon altered defined paths of the rod 14. For example, if the medical dispensing device 10 is altered to enable increased distal movement of the rod 14 without a corresponding increase in enabled proximal movement, then the rate at which pressure on the material reservoir 55 is released upon the release of the trigger 26 will be relatively higher as a result of the alteration (e.g., in comparison to the rate at which pressure on the material reservoir 55 was released upon release of the trigger 26 before the alteration).

The medical dispensing device 10 may include a release button 40 in some examples, where the release button 40 is configured to reduce or substantially eliminate forces that retain components of the medical dispensing device 10 in respective resulting positions, enabling these components to be returned to respective initial positions. For example, the release button 40 may reduce or substantially eliminate forces upon the rod 14 and/or the second engager 16, enabling the rod 14 and/or second engager 16 to be moved (e.g., by a user) to positions that the rod 14 and second engager 16 occupied before the trigger 26 was actuated. The release button 40 may be configured to operate by exerting a distal force upon the retaining member 32. The release button 40 may be configured to be actuated by being pressed into the housing 20, such that the release button 40 pivots around a central pivot point, forcing an arm 60 of the release button 40 to rotate away from the rod 14 and provide a distal force onto the retaining member 32. Alternatively, the release button 40 may be configured to be actuated by sliding the release button 40 distally relative to the housing 20 within a track of the housing 20. When the release button 40 is slid distally along the housing 20, an arm 60 of the release button 40 may provide a distal force onto the retaining member 32.

The release button 40 may be formed from any suitable material, such as, but not limited to, a polymer or a metal. In some examples, a portion of the release button 40 that protrudes from the housing 20 may be coated with or otherwise made of a material that is relatively soft or tacky in order to help a user grip the button 40.

Figure 2:
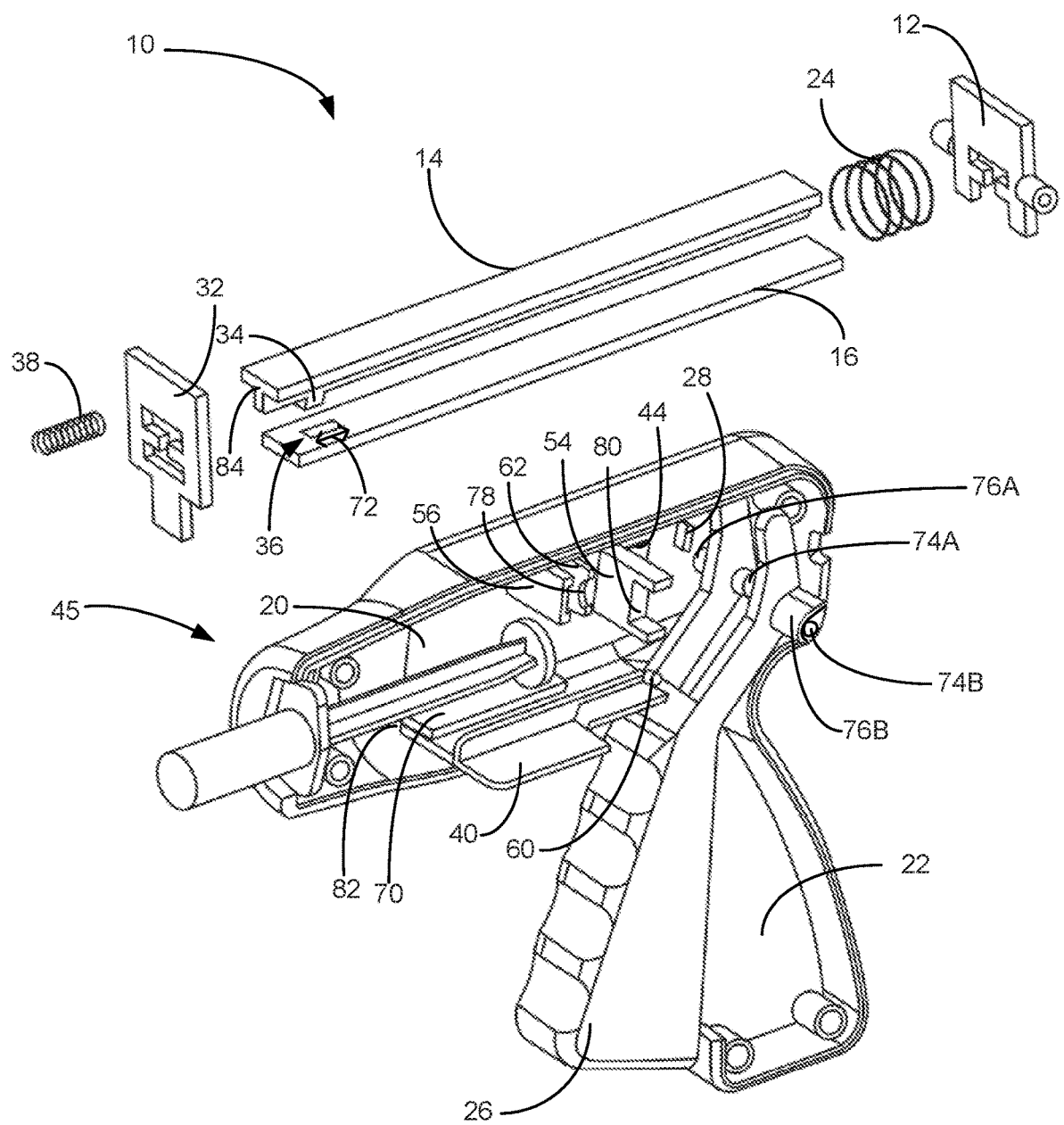
FIG. 2 depicts a cross-sectional, exploded perspective view of the medical dispensing device of FIG. 1.

FIG. 2 depicts a cross-sectional, exploded perspective view of the medical dispensing device 10. In the view shown in FIG. 2, one half of the housing 20 is removed from the view. As discussed above, the flanges 76A-B (collectively "flanges 76) of the trigger 26 are configured to rotate around the rods 74A-B (collectively "rods 74") of the housing 20. The rods 74 may be configured to extend radially in from the housing 20 towards the trigger 26. The flanges 76 may be configured to wrap around the rods 74. In this way, the rods 74 may be configured to become the pivot point of the trigger 26 as the trigger is rotating into/toward the handle 22 and away from the handle 22.

As some of the components (e.g., the first engager 12, the rod 14, the second engager 16, the first compression spring 24, the retaining member 32, the second compression spring 38) of the medical dispensing device 10 are removed from the housing 20 in FIG. 2, the supports 56, 62, 54, 44, 28 of the components may be seen more clearly. For example, the supports 56, 62 for the second compression spring 38, the support 54 for the first compression spring 24, and distal hard stop 44, and proximal hard stop 28 are depicted. In some examples, some of the supports 56, 62, 54 shown in FIG. 2 extend radially across the entirety of the housing 20. Two of these supports 62, 54 may define respective holes 78, 80 configured to receive another component of medical dispensing device 10. For example, the support 62 defines a hole 78, which is configured to prevent radial displacement of the second compression spring 38 relative to the housing 20. The second compression spring 38 may be arranged within this hole 78. As another example, the support 54 for the first compression spring 24 defines a hole 80 through which the rod 14 and the second engager 16 extend. The hole 80 may be configured to prevent non-axial movement of the rod 14 and the second engager 16 as discussed herein. The relative location and radial lengths (e.g., lengths of a support extending from the side of the housing 20 radially into the hollow interior of the housing 20) of the supports are for illustrative purposes only; it is to be understood that other support locations and lengths are possible and contemplated.

As can be seen in the exploded view, the rod 14 includes a general "T" shape with a longitudinal axis and a tab 34. As depicted, the tab 34 may be configured to be received by the slot 36 of the second engager 16. Dimensions of the slot 36 may be altered for different applications. For example, a length 72 of the slot 36 (measured in a direction along a longitudinal axis of the second engager 16) may be lengthened or shortened to suit different applications of the medical dispensing device 10, such as varying the amount of material dispensed or the rate at which it is dispensed.

In the example shown in FIG. 2, the release button 40 is configured to slide axially toward a distal portion 45 of the medical dispensing device 10. The release button 40 is configured to slide within a track 82 as defined by a shelf 70 that extends radially inwards from a side of the housing 20. In some examples, the depicted shelf 70 may be mirrored by a second shelf 70 (not depicted) that extends from the opposite side of the housing 20 and on the opposite side of the release button 40 to complete the track 82.

FIGS. 3A-3B depict a cross sectional view and detail view 90, respectively, of a partially-actuated example medical dispensing device 10. The trigger 26 of the partially actuated medical dispensing device 10 may be partially actuated/pivoted into the handle 22 in the view shown in FIGS. 3A and 3B. As shown in FIG. 3A, in some examples, pushing the trigger 26 proximally into the handle 22 causes the trigger 26 to actuate the first engager 12 such that the first engager 12 is engaged with (e.g., is in contact with) the rod 14. In some examples, the first engager 12 may be configured to only engage the rod 14 when the first engager 12 is not in contact with the proximal hard stop 28. In some examples, the first engager 12 does not engage with the rod 14 until the first engager 12 rotates to a certain angle 100 as discussed herein. The angle 100 may relate to the rotation of the first engager 12 relative to a plane 102 that is parallel with a distal face 84 of the rod 14 as seen in FIG. 2. The rotation of the first engager 12 creates an interference fit between the first engager 12 and the rod 14 (i.e., the rod 14 prevents further rotation of the first engager 12).

In the example shown in FIGS. 3A-3B, the rod 14 and the second engager 16 are in initial positions, as the trigger 26 has not yet actuated sufficiently for the first engager 12 to move the rod 14. Therefore, as seen in the detail view 90 of FIG. 3B, the proximal surface 98 of the tab 34 may be in contact with the proximal surface 94 of the slot 36, and, at the same time, the distal surface 96 of the tab 34 may not be in contact with the distal surface 92 of the slot 36. Specifically, there may be a distance 104 between the distal surface 96 of the tab 34 and the distal surface 92 of the slot 36. For example, this distance 104 may be 0.75 millimeters. It is to be understood that all actual dimensions provided in this disclosure are provided for purposes of illustration only and are not to be interpreted as limiting; other possible dimensions are contemplated and possible. The space between the distal surface 96 of the tab 34 and the distal surface 92 of the slot 36 may enable the tab 34 (and therein the rod 14) to distally move the distance 104 before encountering the distal surface 92 of the slot 36 (and therein the second engager 16).

The retaining member 32 may be configured to engage with the second engager 16 such that the retaining member 32 does not enable the second engager 16 to move axially towards the proximal portion 42 of the housing 20. In some examples, the retaining member 32 is configured to enable axial movement of the second engager 16 towards the distal portion 45 of the medical dispensing device 10, even while the retaining member 32 blocks axial movement in the proximal direction. The retaining member 32 may be configured to avoid contact with the rod 14 as discussed in greater detail herein.

FIGS. 4A-4B depict a cross sectional view and detail view 110, respectively, of the medical dispensing device 10 in a fully actuated state. The trigger 26 of FIG. 4A may be fully actuated. As such, the first engager 12 has distally moved toward the distal portion 45 of the medical dispensing device 10 until the first engager 12 is engaging the distal hard stop 44 as discussed in more detail in FIGS. 6A-6C. For example, the first engager 12 may have distally moved 3.25 millimeters in response to a distal force from the trigger 26 in FIG. 3A. Put differently, there may 3.25 millimeters between the proximal hard stop 28 (obscured by trigger 26) and the distal hard stop 44 after accounting for the width of the first engager 12. As a result, the first engager 12 may distally move the rod 14 toward the distal portion 45 of the medical dispensing device 10. In some examples, there is a one-to-one correlation between distal movement of the first engager 12 and movement of the rod 14, such that the rod 14 has likewise moved 3.25 millimeters.

As depicted in detail view 110 of FIG. 4B, the distal surface 96 of the tab 34 is now engaged with the distal surface 92 of the slot 36. As the first engager 12 and the rod 14 moved axially 3.25 millimeters and there was a distance 104 of 0.75 millimeters (in an example) between the distal surface 92 of the slot 36 and the distal surface 96 of the tab 34, the tab 34 may have engaged the distal surface 92 of the slot 36 after moving 0.75 millimeters (or another distance 104 in other examples). In some examples, the distance 104 is a threshold, such that any trigger 26/first engager 12/rod 14 movement in the axial direction less than the distance 104 will not actuate the second engager 16. Being as axial movement of the rod 14 less than the distance 104 threshold may not actuate the second engager 16, that may mean that within this threshold (e.g., while axially moving distances less than distance 104) the trigger 26/first engager 12/rod 14 may actuate back and forth substantially perpetually without further limitations (e.g., limitations beyond the distance 104 and the proximal hard stop 28).

After the rod 14 distally moves distance 104, the rod 14 may effectively push the second engager distally an overpressurization distance 106 (see FIG. 3A). The overpressurization distance 106 is the distance that the first engager 12 may axially move after the distance 104 before the first engager 12 engages the distal stop 44 to overpressurize the material as described herein. In the example above, the overpressurization distance 106 is 0.75 millimeters, as this is the distance that the rod 14 will move once the trigger 26 is released to release the pressure. As the first engager 12 moves the full overpressurization distance 106 the material of the medical dispensing device 10 is overpressurized as described herein such that the material is dispensed faster.

In some examples, the amount of force that is required to actuate the trigger 26 during the first distance 104 of actuation (an amount of force greater than the spring force of the first compression spring 26, as determined by Hooke's law) may be less than the amount of force required to actuate the trigger 26 during the pressurization distance 106, as the second engager 16 must be pushed along with the first compression spring 24 overpowered. The amount of power required to actuate the overpressurization distance 106 may be further increased in examples in which the second engager 16 must overcome some static or dynamic friction with the retaining member 32 while distally moving. In some examples, moving the rod 14 distally a distance that results in such overpressurization (e.g., requiring a higher amount of force than is physically necessary to push out the viscous liquid using the rod 14) may result in a steadier flow rate, as a fluid nature of the viscous liquid may no longer be the limiting factor.

As depicted in FIG. 4A, relative to the initial position shown in FIG. 3A, the second engager 16 may have moved axially overpressurization distance 106 towards the distal portion 45 of the medical dispensing device 10. Also, as depicted in the detail view 110, there is currently a distance 104 (e.g., 0.75 millimeters) between the proximal surface 98 of the tab 34 and the proximal surface 94 of the slot 36. Therefore, the proximal surface 98 of the tab 34 (and therein the rod 14) may axially move towards the proximal portion 42 of the medical dispensing device 10 the distance 104 before engaging the proximal surface 94 of the slot 36. Further, in the state of the medical dispensing device 10 shown in FIG. 4A, the second engager 16 may be engaged with the retaining member 32 that is configured to block axial movement of the second engager 16 towards the proximal portion 42 of the medical dispensing device 10. As such, the second engager 16, as depicted in FIG. 4B, is in the actuated position. As described herein, the actuated position may be the position of the second engager 16 after the rod 14 has been actuated at least the threshold distance (e.g., distance 104), at which point the second engager 16 blocks proximal movement of the rod 14 beyond the distance 104.

FIGS. 5A-5B depict a cross sectional view and detail view 120, respectively, of the medical dispensing device 10 after it has been fully actuated and released, thus, after the full actuated state shown in FIGS. 4A and 4B. The medical dispensing device 10 being released from actuation may include an operator (e.g., a human who is using medical dispensing device 10) reducing or eliminating the force that is exerted upon the trigger 26 toward the handle 22. In response to such pressure being reduced, the first engager 12 is configured to move into contact with the proximal hard stop 28. In some examples, the first engager 12 is in contact with the proximal hard stop 28 as a result of the first compression spring 24 exerting a proximal force upon the first engager 12. The trigger 26 may be pivoted away from the handle 22 as far as enabled by the geometry of the medical dispensing device 10. In some examples, the trigger 26 may have pivoted away from the handle 22 in response to a proximal force exerted upon the first portion 52 of the trigger 26 by the first compression spring 24 via the first engager 12. The proximal force from the first compression spring 24 may be converted to a rotational force around the rods 74 of the housing 20.

The second engager 16 remains in substantially the same axial position when the trigger 26 is released in FIG. 5A. The second engager 16 may have remained in the same position as a result of the retaining member 32 that is configured to limit axial movement of the second engager 16 towards the proximal portion 42 of the housing 20. As depicted in the detail view 120 of FIG. 5B, the proximal surface 98 of the tab 34 may be engaged with the proximal surface 94 of the slot 36. This means that the tab 34, and therefore the rod 14, axially moved the distance 104 towards the proximal portion 42 of the housing 20. Upon moving the distance 104 to engage with the second engager 16, the second engager 16 is configured to block the rod 14 from further axially movement towards the proximal portion 42 of the housing 20. The rod 14 may not be able to move as the tab 34 is engaged with the slot 36 of the second engager 16, and the second engager 16 is engaged with the retaining member 32.

The retaining member 32 may be configured to limit the proximal movement of the second engager 16 as a result of retaining member 32 being arranged at the angle 125 as depicted in FIG. 5A. As the release button 40 is slid distally along the housing 20, the arm 60 of the release button 40 may be configured to engage and distally move the retaining member 32. The arm 60 may be configured to make the retaining member 32 more parallel to a distal face 84 of the rod 14 as seen in FIG. 2. As the retaining member 32 becomes substantially parallel to the distal face 84 of the rod 14, the retaining member 32 may disengage the second engager 16. As the retaining member 32 disengages the second engager 16, the second engager 16 may be enabled to move proximally freely (e.g., as a result of an operator grabbing the pulling the second engager 16 proximally). In some examples (not depicted), the medical dispensing device 10 may be configured (e.g., with compression springs) to automatically return the second engager 16 and/or rod 14 to an initial position.

Figure 6B:
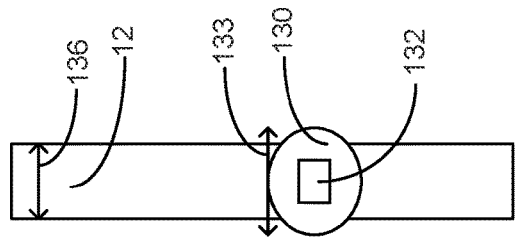
FIGS. 6A-6C depict a front, side, and top view of an example first engager, respectively.
Figure 6A:
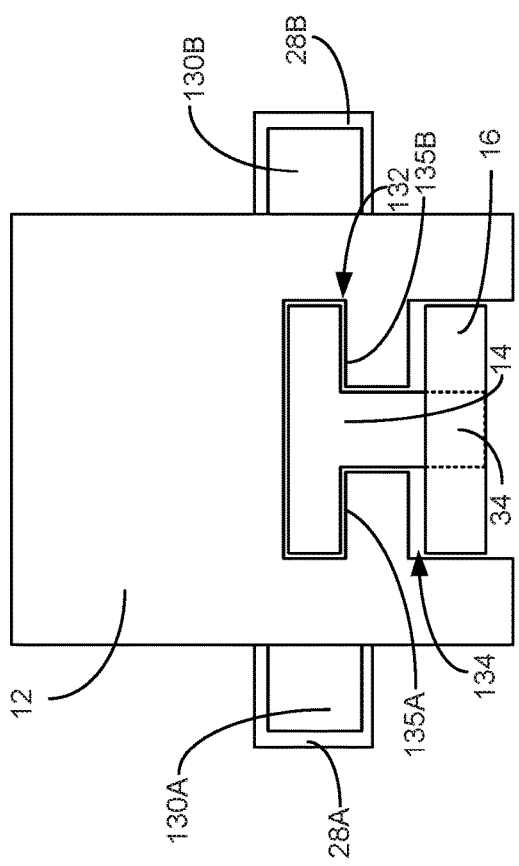

FIG. 6A depicts a front view of an example first engager 12. FIG. 6A may depict the first engager 12 from the perspective of the distal portion 45 oriented towards the proximal portion 42. The first engager 12 is configured to be a first distance 132 away from the rod 14 before the trigger 26 is actuated. The first distance 132 may be the smallest distance that is between a surface of the first engager 12 and a surface of the rod 14 before the trigger 26 is actuated, wherein the surface of the engager 12 and the surface of the rod 14 will physically contact each other after the trigger 26 is actuated. The first engager 12 is likewise configured to be a second distance 134 away from the second engager 16 before the trigger 26 is actuated. The second distance 134 may be greater than the first distance 132, such that when the trigger is actuated 26 to a point where the first engager 12 rotates to an angle 100 (shown in FIG. 3A) towards the rod 14, the first engager 12 will engage the rod 14 and not the second engager 16. Internal surfaces 135A-B (collectively "internal surfaces 135") of the first engager 12 may be treated to better engage the rod 14. For example, the internal surfaces 135 may be treated or coated with a substance that is relatively tacky, such that the substance increases the amount of relative static/dynamic friction between the first engager 12 and the rod 14. In addition to, or instead of, the surface treatment or coating, the internal surfaces 135 may be physically etched or otherwise altered to configure the internal surfaces 135 to better engage the rod 14.

Two first engager knobs 130A-B (collectively "first engager knobs 130") are configured to engage with respective proximal hard stops 28A, 28B and distal hard stops 44A, 44B (shown in FIG. 6C) for the first engager 12. In some examples, as depicted in FIG. 6A, the first engager knobs 130 may have a smaller profile than the proximal hard stops 28A, 28B, which might themselves be substantially the same size as the distal hard stops 44. In some examples, the first engager knobs 130 may be part of a single structure with the first engager 12. In other examples, the first engager knobs 130 may be affixed to the first engager 12. The first engager knobs 130 may be affixed to the first engager 12 by any means known to one skilled in the art.

For example, FIG. 6B depicts a side view of an example first engager 12. FIG. 6B depicts the example first engager 12 as seen in FIGS. 1, 3A, and 4A. Within the side view, a pin 132 is affixing a first engager knob 130 to a first engager 12. The first engager knob 130 may have a diameter 133 or other outer dimension that is greater than a width 136 of the first engager 12.

Figure 6C:
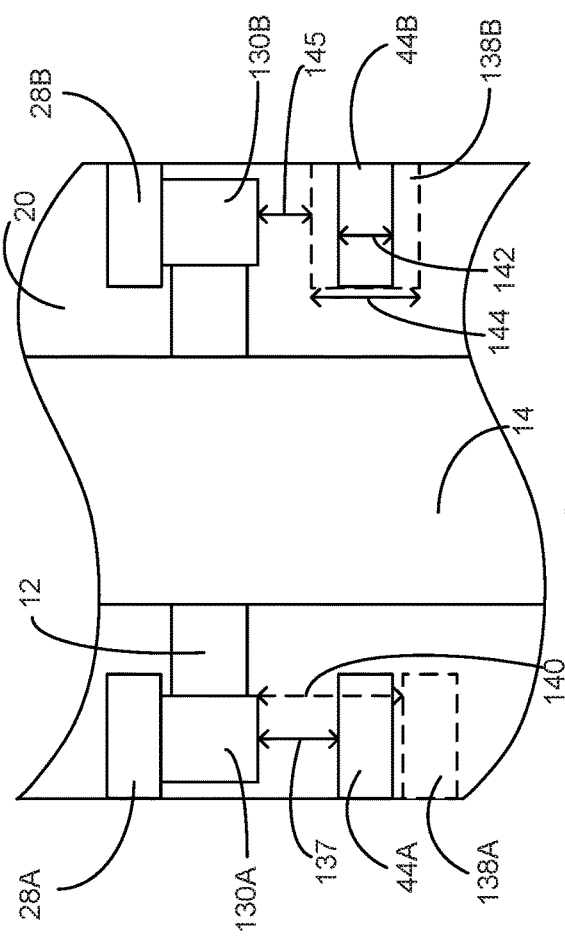

FIG. 6C depicts a top view of an example first engager 12. FIG. 6C depicts the first engager 12 as seen from the general area of the handle 22 oriented toward the housing 20. The first engager 12 may move axially between the proximal hard stops 28A, 28B and the distal hard stops 44A, 44B. The first engager 12 may move a distance 137 between the proximal hard stops 28 and the distal hard stops 44. In some examples, a user may modify the distance 137. For example, the distal hard stop 44 may be configured to be removed from the housing 20 and reinserted at different locations along the housing 20. For example, the distal hard stops 44A, 44B may be moved to respective new locations 138A, 138B that are each closer to the distal portion 45 of the housing 20. Alternatively, the distal hard stops 44A, 44B may be moved by sliding the distal hard stops 44A, 44B along the housing 20 via a slide (not shown) on the outside of the housing 20. The slide may move along detents that provide defined movement increments (for example, 0.1 inches, 0.2 inches, 0.25 inches, etc.). Further still, the slide may move freely along a slot any distance, and the slide may be a thumb screw that is configured to be loosened to move the slide and tightened to be retained in a specific location. In any event, by moving the distal hard stops 44A, 44B to the new location 138 the first engager 12 may be able to move a distance 140, which is greater than distance 134 with the prior position of the distal hard stops 44A, 44B.

Increasing the distance that the first engager 12 may travel (e.g., moving the distal hard stop to the new location 138) may result in an increased aliquot of the material and/or increased overpressurization of the material during dispensing, depending upon whether or not the slot 36 in the second retainer 16 is increased accordingly. For example, if the distance that the first engager 12 may travel is increased (e.g., by changing from distal hard stop 44B to distal hard stop 138B) while the slot 36 has the same length, the rod 14 may move distally more and move proximally the same amount, resulting in both more pressure and more dispensed material. For another example, if the distance that the first engager 12 may travel and the length 72 of the slot 36 are both increased the same amount, the rod 14 may move distally more but conclude in the same actuated position, resulting in more pressure but the same aliquot of material. In this way, an operator may modify first engager 12 travel distances and lengths 72 of slot 36 to configure a medical dispensing device 10 to have a desired overpressurization amount and predetermined material aliquot.

In other examples, the distance that the first engager 12 can travel is not altered by changing the location of a set of distal hard stops 44, but instead by switching a first set of distal hard stops 44A, 44B each having a first width 142 with a second set of distal hard stops each having a second width 144. If, as depicted, the second set of distal hard stops have a second width 144 that is twice as wide as the first width 142 of the first set of distal hard stops 44A, 44B, the distance 145 that the first engager 12 can axially move may be shortened. Configuring the frame 20 and the hard stops 28, 44 that define the enabled movement of the first engager 12 such that the distance that the first engager 12 may axially move is alterable may provide versatility to the medical dispensing device 10, as the medical dispensing device 10 may be therein configured to deliver predetermined aliquots of material with each full actuation of the medical dispensing device (e.g., full press of the trigger 26 until the first engager 12 engages the distal hard stop 44, and full release of the trigger 26 until the first engager 12 engages the proximal hard stop 28. In addition, configuring the medical dispensing device 10 such that the position of the stops 44A, 44B may be modified may enable the device 10 to be used with different sized syringes (e.g., syringes holding different maximum volumes of material), as different distances 145 may be required to dispense the desired aliquots from different sized syringes.

Figure 7A:
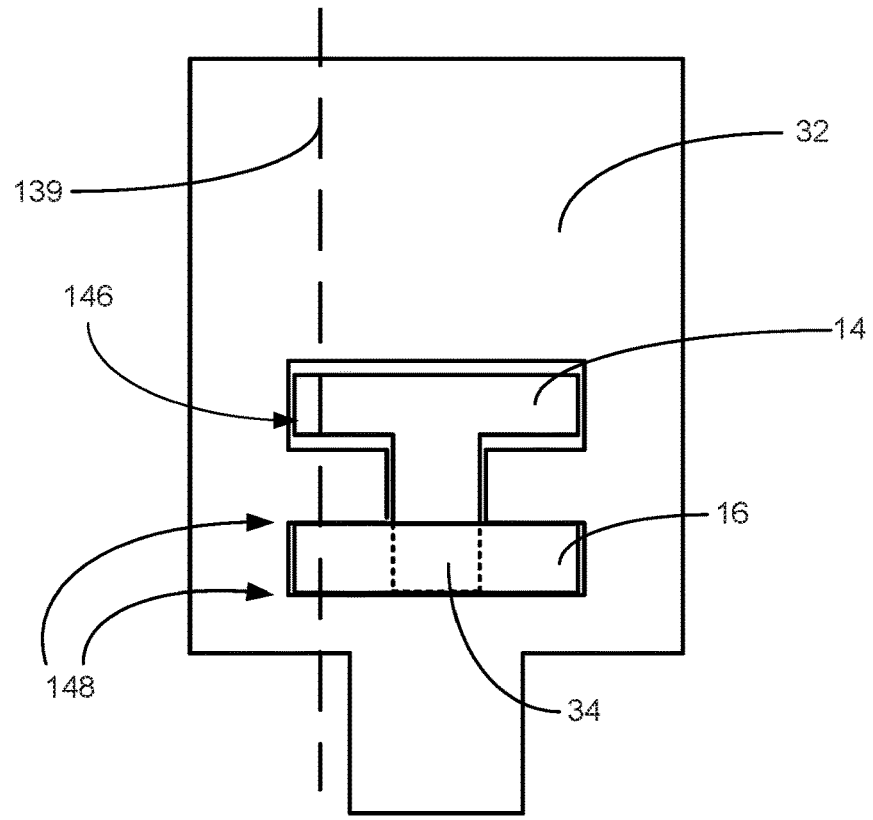
FIGS. 7A-7B depict a front view and cross-sectional side view, respectively, of an example retaining member.

FIG. 7A depicts a front view of an example retaining member 32. FIG. 7A depicts the retaining member 32 when the retaining member 32 is at an angle 125 as depicted in FIG. 5A. As discussed above, in some examples the retaining member 32 restricts the second engager 16 from moving towards the proximal end 42 of the medical dispensing device 10. The retaining member 32 is configured to be a first distance 146 away from the rod 14. In some examples, the retaining member 32 is configured such that the first distance 146 remains substantially constant throughout the actuation of the trigger 26 (e.g., as a result of the retaining member 32 remaining at the angle 125), such the retaining member 32 never engages the rod 14. The retaining member 32 is likewise configured to be a second distance 148 away from the second engager 16. In some examples, the second distance 148 may be substantially zero (e.g., zero or nearly zero), such that the retaining member 32 is virtually always engaged with the second engager 16 as long as the retaining member is at the angle 125. In some examples, the retaining member 32 is configured to engage with the second engager 16 such that the retaining member 32 always enables the second engager 16 to axially move toward the distal portion 45 of the housing 20. Further, in some examples the retaining member 32 is configured to engage with the second engager 16 such that the retaining member 32 blocks the second engager 16 from axially moving toward the proximal portion 42 of the housing 20.

In some examples, a medical dispensing device 10 may be configured such that a second engager 16 may move both proximally and distally, rather than just distally as in some examples of medical dispensing device 10. A second engager 16 may be able to move proximally due to the respective medical dispensing device 10 not including a retaining member 32 that is configured to block proximal movement of the second engager 16 in place. Instead, the second engager 16 may move proximally as pushed by a spring until the second engager 16 encounters a hard stop, and the second engager 16 may move distally as pushed by the transfer movement assembly 35.

Figure 7B:
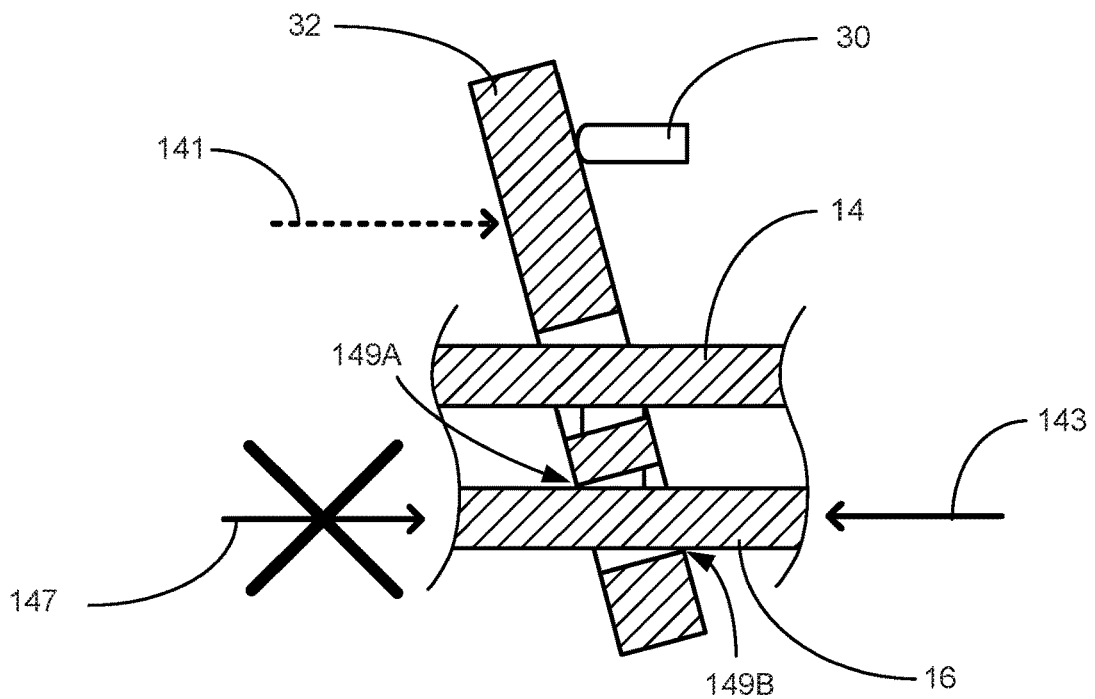

FIG. 7B depicts a cross-sectional side view taken along a plane 138 of FIG. 7A. As depicted in FIG. 7B, the retaining member 32 does not engage the rod 14, though internal corners 149A, 149B (collectively "internal corners 149") of the retaining member 32 are engaging second engager 16. The retaining member 32 undergoes a proximal force 141 (e.g., a force 141 that pushes the retaining member 32 proximally) from the second compression spring 38. The retaining member 32 is also blocked from proximal movement by the second engager hard stop 30 that defines the proximal-most position of the retaining member 32 as described herein. The retaining member 32 may be configured to enable distal movement 143 of the second engager 16 in response to a distal force upon the second engager 16. For example, the retaining member 32 may enable distal movement 143 of the second engager 16 in response to a distal force exerted by the second engager 16 upon the internal corners 149 sufficient to overpower the proximal force exerted upon the second engager 16 by the internal corners 149 as a result of the proximal force 141. However, the retaining member 32 may be configured to block proximal movement 147 of the second engager 14. For example, the retaining member 32 may be configured to block proximal movement 147 of the second engager 16 due to the relatively high static friction the internal corners 149 exert upon the second engager 16 as the retaining member 32 is pressed against the second engager hard stop 30.

Figure 8:
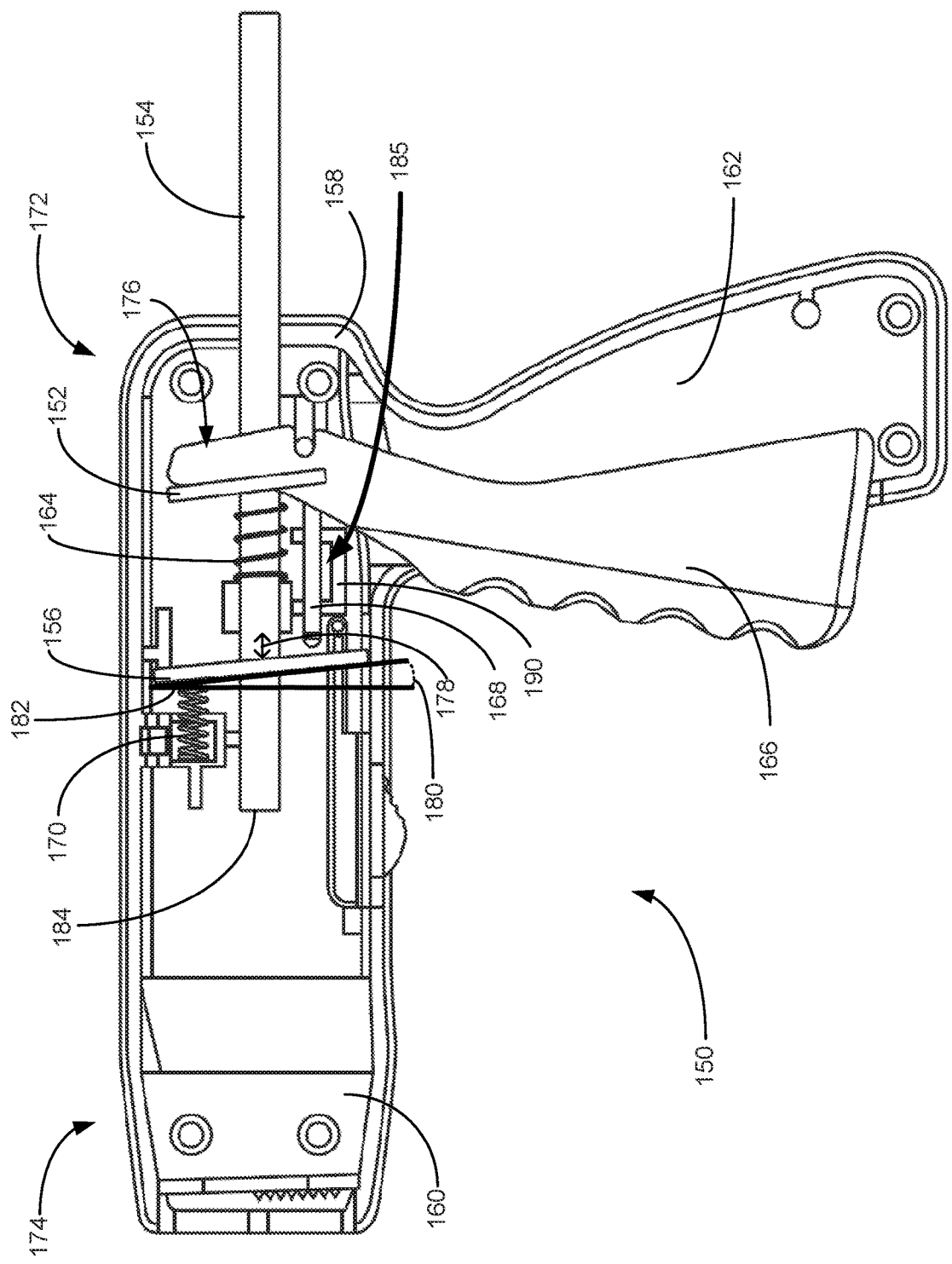
FIG. 8 depicts a cross-sectional view of a partially-actuated example medical dispensing device.

FIG. 8 depicts a cross-sectional view of a partially-actuated example medical dispensing device 150. The medical dispensing device 150 may be substantially similar to the medical dispensing device 10 except in regard to the specific differences described herein. The medical dispensing device 150 includes a frame 158 with a housing 160 that houses a rod 154 and a handle 162 that extends from a proximal portion 172 of the housing 160. A first engager 152 may be substantially similar to the first engager 12, though in some examples the first engager 152 may not be configured to maintain a distance 134 relative to a second engager 16 as discussed in FIG. 6A. The first engager 152 may be located distal to a trigger 166 of the medical dispenser device 150. In the example shown in FIG. 8, the first engager 152 is distal to a first portion 176 of the trigger 166. The first engager 152 is pressed against the trigger 166 by a first compression spring 164. Similar to the medical dispensing device 10 above, as the trigger 166 pivots in towards the handle 162 the first engager 152 may axially move (in a direction along a longitudinal axis of the rod 154) towards a distal portion 174 of the housing 160. Further, as the trigger 166 pivots out away from the handle 162, the first engager 152 may axially move towards a proximal portion 172 of the housing 160.

A movement transfer assembly 185 of the medical dispensing device 150 that translates movement of the trigger 166 to the rod 154 includes a second compression spring 170 and a transferring member 168. The transferring member 168 protrudes distally into the housing 160 relative to the housing. A second engager 156 is configured to limit axial movement of the rod 154 towards the proximal portion 172 of the housing 160. The second engager 156 may be configured to engage with the rod 154 such that the rod 154 may axially move towards the distal portion 174 of the housing 160 as the second engager 156 moves. The second engager 156 may be configured to engage (e.g., physically contact) the rod 154 similar to how the first engager 12 was configured to engage the rod 14. For example, the second engager 156 may be configured to engage the rod 154 when the second engager 156 is at an angle 180 from a plane 182 that is parallel to a distal surface 184 of the rod 154, thereby preventing proximal movement of the rod 154. Similarly, the second engager 156 may be configured to not engage with the rod 154 as the angle 180 is reduced and the second engager 156 approaches being planar with the plane 182, thereby enabling distal movement of the rod 154.

The transferring member 168 may be a distance 178 away from the second engager 156. In some example, the distance 178 may be the threshold amount described above, wherein, if the trigger 166 does not pivot at least the threshold amount into/toward the handle 162, the second engager 156 will not axially move, even as the other components (e.g., the trigger 166, the first engager 152, and the rod 154) of the medical dispensing device 150 move axially in either distal or proximal directions. As used herein, the threshold distance that the trigger 166 must pivot into the handle 162 may be a linear distance (e.g., rather than a rotation distance). Further, in some examples the threshold distance is from a distal surface of the trigger 166 relative to the handle 162. In some examples, the second engager 156 may be engaged with the rod 154 until the transferring member 168 axially moves the distance 178 as discussed herein. For example, the second engager 156 may engage the rod 154 such that the rod 154 may axially move towards the distal portion 174 of the housing while not being able to axially move towards the proximal portion 172 of the housing 160. Further, in certain examples, the second engager 156 may still provide a relatively small amount of proximal force upon the rod 154 as the rod 154 is moving towards the distal portion 174 of the housing 160, resulting in additional overpressurization of the rod 154 as discussed herein. Together, this configuration may result in the medical dispensing device 150 moving the rod 154 distally a predetermined first amount upon fully actuating the trigger 166 and then moving the rod proximally a predetermined second amount upon release the trigger 166, wherein the second amount is smaller than the first amount.

The transferring member 168 may be held in place by a support 190 that is configured to block all non-axial movement of the transferring member 168. The transferring member 168 may be affixed to the trigger 166, such that as the trigger 166 pivots into the handle 162 the transferring member 168 axially moves toward the distal portion 174 of the housing 160, and as the trigger 166 pivots away from the handle 162 the transferring member 168 axially moves towards the proximal portion 172 of the housing 160. In some examples, the transferring member 168 is a pin or dowel that is pressed into a hole of the trigger 166.

Figure 9:
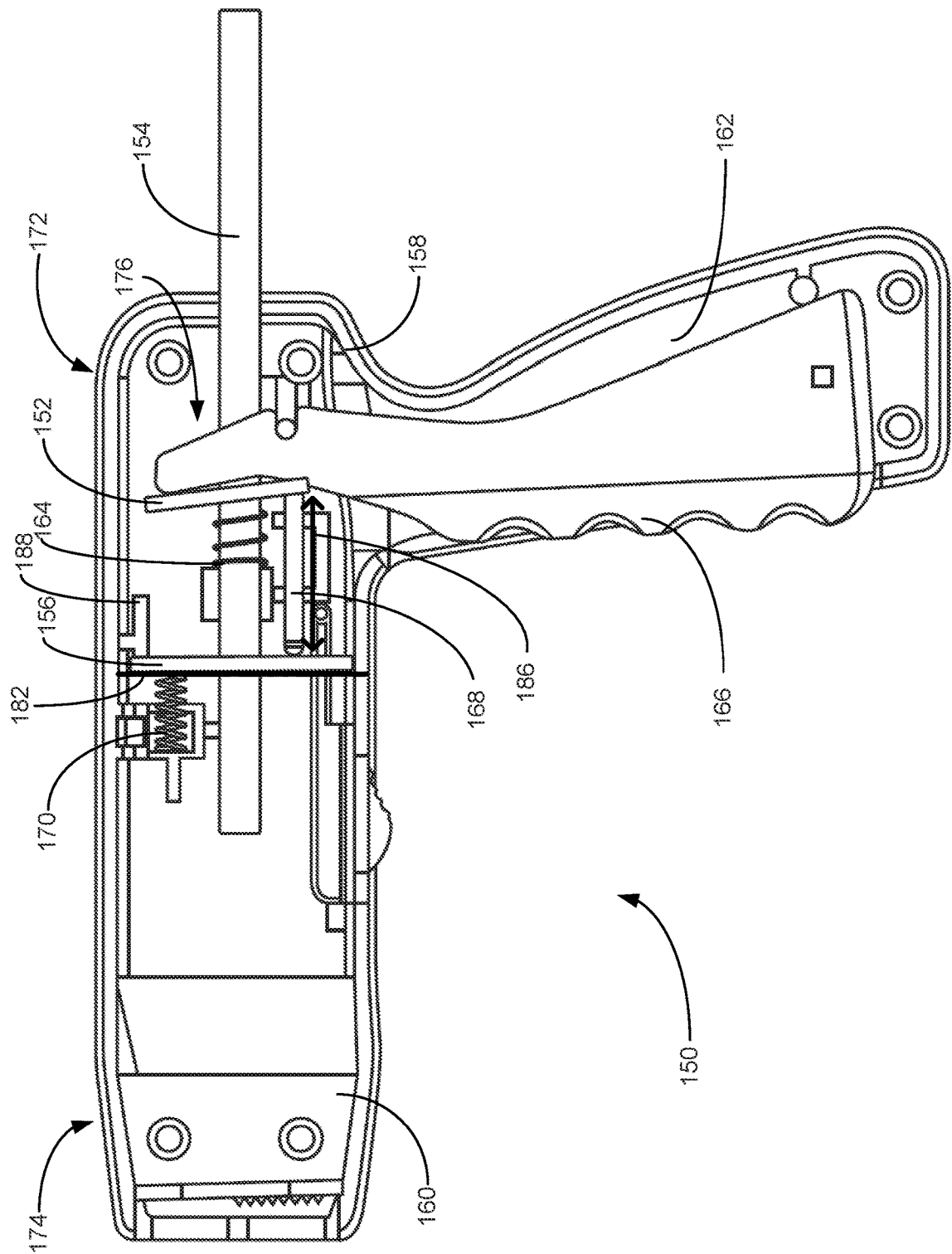
FIG. 9 depicts a cross-sectional view of a fully-actuated example medical dispensing device.

FIG. 9 depicts a cross-sectional view of the medical dispensing device 150 in a fully actuated state. The transferring member 168 axially moved the distance 178 as the trigger 166 was actuated. Upon moving the distance 178, the transferring member 168 may be configured to engage the second engager 156. The second engager 156 may be configured to disengage the rod 154 immediately upon or soon after being engaged by the transferring member 168. In some examples, engaging the second engager 156 may include the transferring member 168 physically touching and then exerting a distal force upon a proximal surface of the second engager 156. Upon engaging the second engager 156, the transferring member 168 may be configured to move the second engager 156 axially towards the distal portion 174 of the housing 160. When the transferring member 168 is fully actuated (e.g., when the trigger 166 is fully depressed into the handle 162), the transferring member 168 may move the second engager 156 such that second engager 156 is substantially parallel with the plane 182. The amount that the transferring member 168 is configured to move the second engager 156 may be defined by a length 186 of the transferring member 168.

As a force upon the trigger 166 is reduced or substantially eliminated (e.g., as a result of a human operator letting go off or reducing a "grip" on the trigger 166), the first compression spring 164 may act upon the first engager 152 to push the trigger 166 back to an initial position, where the trigger 166 is pivoted out away from the handle 162, similar to the same components of the medical dispensing device 10 discussed above. Further, the second compression spring 170 may be configured to push the second engager 156 against a second engager hard stop 188 to an actuated position, which in some examples is the initial position of FIG. 8. As the second engager 156 moves axially towards the proximal portion 172 of the housing 160, the second engager 156 re-engages the rod 154. Upon re-engaging the rod 154, the second engager 156 limits axial movement of the rod 154 towards the proximal portion 172 of the housing 160. This may result, upon full actuation and subsequent release of the medical dispensing device 150 (e.g., full depression of the trigger 166 into the handle 162 followed by reduction or elimination of the pressure upon the trigger 166), in the rod 154 moving distally a distance substantially equal to the distal distance travelled by the first engager 152 (e.g., similar to the distance 134 of FIG. 6C) followed by the rod 154 moving proximally a predetermined distance substantially equal to the proximal distance traveled by the second engager 156.

In some examples, a medical dispensing device may be configured such both the trigger and the second engager are proximal to the handle. In such examples, the trigger may pivot in towards the handle in a distal direction, and the trigger may pivot away from the handle in a proximal direction. The second engager may be able to move in both a proximal and a distal direction. The second engager may move proximally as pushed by a spring until the second engager encounters a hard stop, and the second engager may move distally as pulled by the transfer movement assembly. Further, in some examples a housing is configured to be generally cylindrical (e.g., rather than being generally a rectangular cuboid, which is also possible), such that the housing has a circular cross-section.

Figure 10:
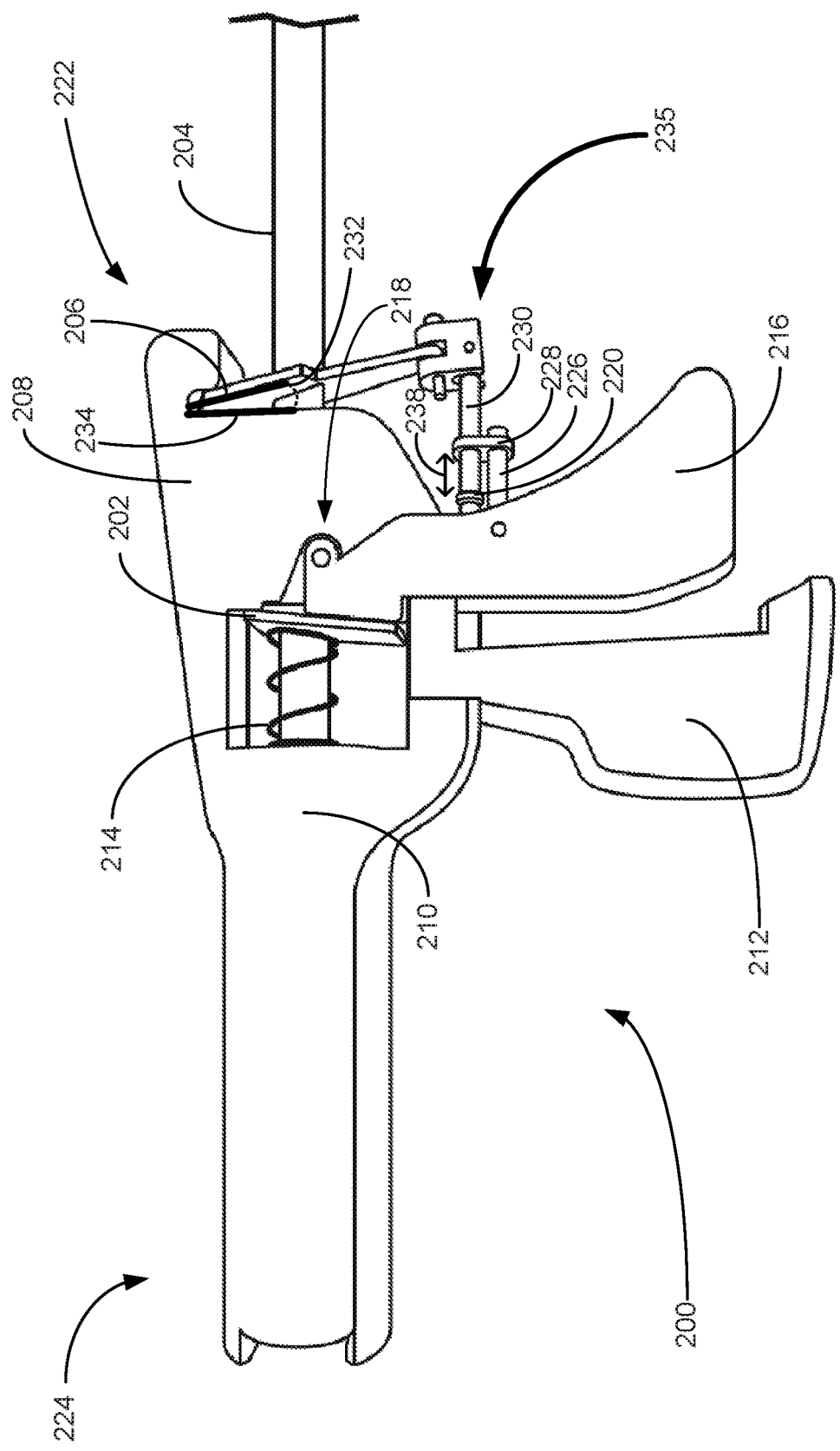
FIG. 10 depicts a side view of an example medical dispensing device.

FIG. 10 depicts a side view of an example medical dispensing device 200. The medical dispensing device 200 may be substantially similar to the medical dispensing device 10 except in regard to the specific differences described herein. The medical dispensing device 200 includes a frame 208 with a housing 210 that houses a rod 204. The frame 208 may further include a handle 216 that extends from a proximal portion 222 of the housing 210. A trigger 216 is configured to pivot axially into and away from the handle 212. A first engager 202 may be substantially similar to the first engager 12, though in some examples the first engager 202 may not be configured to maintain a distance 134 between a second engager 16 as discussed in FIG. 6A.

In the example shown in FIG. 10, the first engager 202 is located distal to the trigger 216. For example, the first engager 202 may be distal to a first portion 218 of the trigger 216. The first engager 202 may be configured to be pressed against the trigger 216 by a first compression spring 214. Similar to the medical dispensing device 10 above, as the trigger 216 pivots in towards the handle 212, the first engager 202 may be configured to axially move towards a distal portion 224 of the housing 210. Further, as the trigger 216 pivots out away from the handle 212 the first engager 202 may be configured to axially move towards a proximal portion 222 of the housing 220.

A movement transfer assembly 235 of the medical dispensing device 200 that transfers movement of the trigger 216 to the rod 204 includes a transferring member 226, an absorbing member 230, and a plate 228. The transferring member 226 extends proximally from the trigger 216. The absorbing member 230 extends distally from the second engager 206. The absorbing member 230 may have a flange 220 on a distal edge. The plate 228 may be affixed to the transferring member 226. The plate 228 may couple the transferring member 226 to the absorbing member 230. The plate 228 may interface with the absorbing member 230 with a hole in the plate 228 that the absorbing member 230 is configured to slide through. The flange 220 of the absorbing member 230 is not configured to fit through the hole in the plate 228. Before the trigger 216 is actuated (e.g., before a distal force is placed upon the trigger 216 by a human operator), there may be a distance 238 between the flange 220 and the plate 228.

A second engager 206 is configured to limit axial movement of the rod 204 in a direction towards the proximal portion 222 of the housing 210. The second engager 206 may be configured to engage with the rod 204 such that the rod 204 may axially move towards the distal portion 224 of the housing 210. The second engager 206 may be configured to engage (e.g., physically contact) the rod 204 similar to how the first engager 12 is configured to engage the rod 14, such that the second engager 206 engages the rod 204 when the second engager 206 is at an angle 232 from a plane 234 that is parallel to a distal surface (e.g., distal surface 236 of FIG. 11) of the rod 204. Similarly, the second engager 206 may be configured to not engage with the rod 204 as the angle 232 is reduced and the second engager 206 approaches being planar with the plane 234. That is, the second engager 206 may be configured to provide a proximal stopping force upon the rod 204 after the rod 204 has moved distally a first amount and proximally a second smaller amount.

Figure 11:
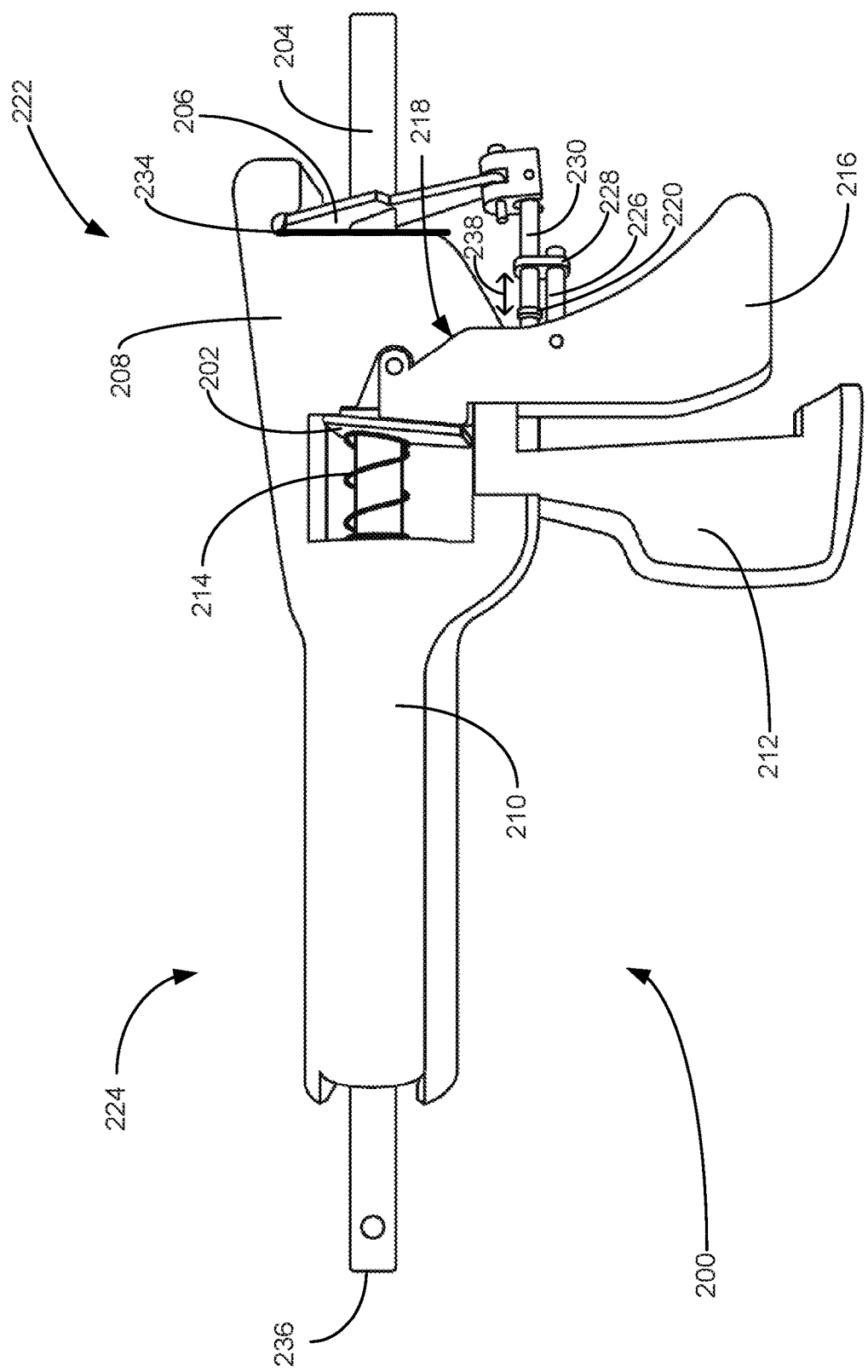
FIG. 11 depicts a side view of a partially-actuated example medical dispensing device.

FIG. 11 depicts a side view of the medical dispensing device 200 in a partially-actuated configuration. As the trigger 216 pivots in towards the handle 212, the first engager 202 is configured to engage the rod 204 as described herein. As the trigger 216 actuates, the first engager 202 may be configured to engage with the rod 204 and provide a distal force upon the rod 204. In examples in which the second engager 206 is configured to enable axial movement of the rod 204 towards the distal portion 224 of the housing 210, the rod 204 may distally move as soon as the first engager 202 thusly engages with the rod 204. As the trigger 216 moves distally towards the handle 212, the transferring member 226 and the plate 228 are configured to move distally relative to the housing 210 and the absorbing member 230. As the trigger 216 (and therein the transferring member 226 and small plate 228) move at least the distance 238, the transferring member 226 is configured to engage with the absorbing member 230 as described herein.

In some example, the distance 238 may be the threshold amount described above. For example, in some examples, if the trigger 216 does not pivot at least the threshold amount into/toward the handle 212 that correlates into the transferring member 226 moving at least the distance 238, the second engager 206 will not axially move, even as the other components (e.g., the trigger 216, the first engager 202, and the rod 204) of the medical dispensing device 200 move axially in either distal or proximal directions. As used herein, the threshold distance that the trigger 216 must pivot into the handle 212 may be a linear distance (e.g., rather than a rotation distance). Further, in some examples the threshold distance is from a distal surface of the trigger 216 relative to the handle 212. In some examples, the second engager 206 may be engaged with the rod 204 until the transferring member 226 axially moves the distance 238 as discussed herein. For example, the second engager 206 may engage the rod 204 such that the rod 204 may axially move towards the distal portion 224 of the housing 210 while not being able to axially move towards the proximal portion 222 of the housing 210. Further, in certain examples the second engager 206 may still provide a relatively small amount of proximal force upon the rod 204 as the rod 204 is moving towards the distal portion 224 of the housing 210, resulting in a slight overpressurization of the material in the material reservoir 58 (not shown in these Figures) by the rod 204 as discussed herein.

Figure 12:
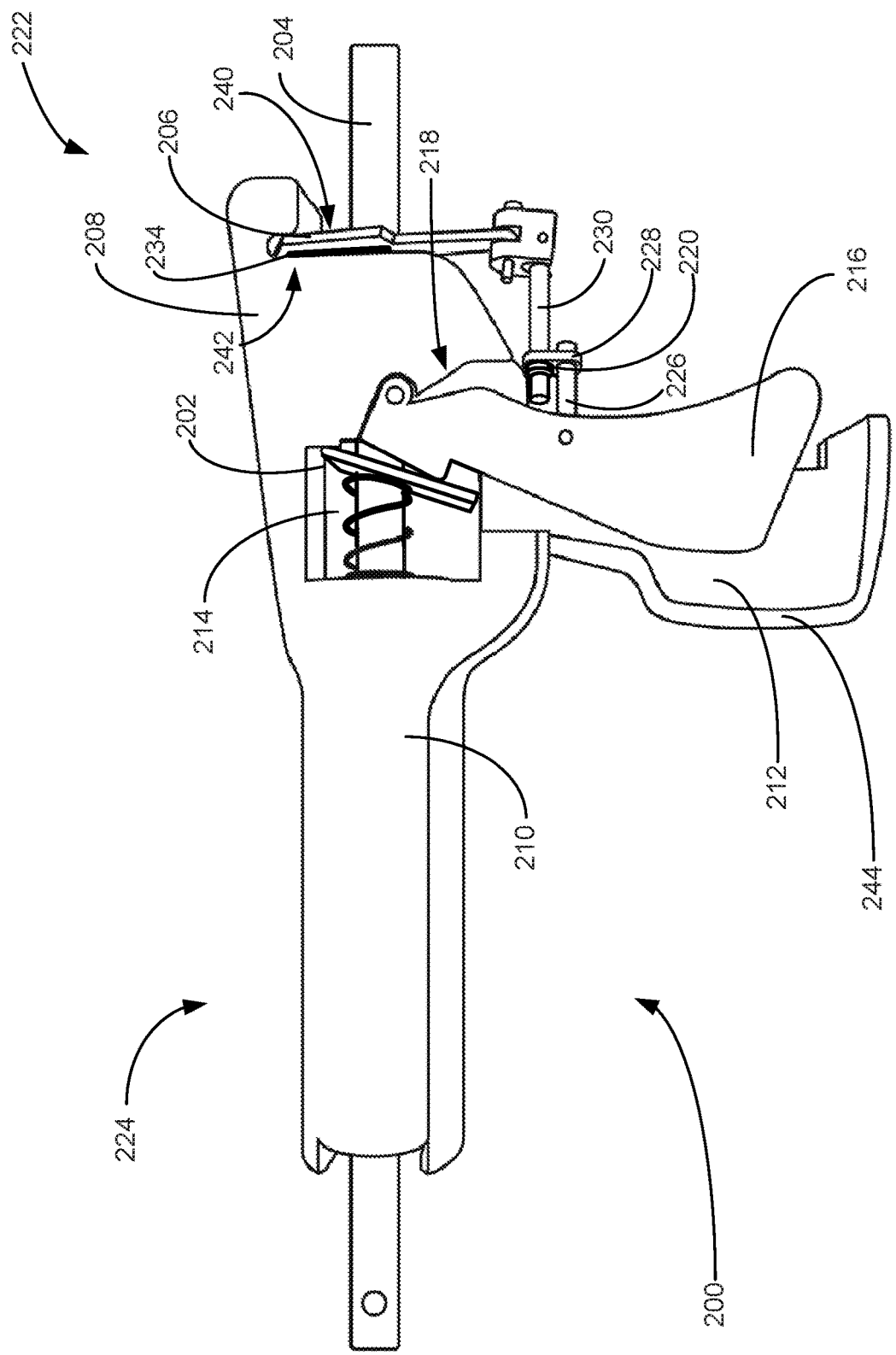
FIG. 12 depicts a side view of a fully-actuated example medical dispensing device.

FIG. 12 depicts a side view of the medical dispensing device 200 in a fully actuated state. The medical dispensing device 200 may be fully actuated when trigger 216 is actuated distally into the handle 212 until the trigger 216 engages with a distal wall 244 of the handle, where the distal wall 244 acts as a hard stop for the distal rotation of the trigger 216. As a result of the trigger 216 engaging the distal wall 244, the first engager 202 (and therein the rod 204) may not be able to move further toward the distal portion 224 of the housing 210. Further, as a result of the trigger engaging the distal wall 244, the transferring member 226 (and therein the absorbing member 230 and second engager 206) may not be able to move further toward the distal portion 224 of the housing 210.

The transferring member 226 moved at least the distance 238 (shown in FIG. 11) such that the plate 228 engages with the flange 220 of the absorbing member 230. Upon engaging the flange 220, the absorbing member 230 may be configured to provide a distal force upon the second engager 206. The distal force of the absorbing member 230 upon the second engager 206 may result in the second engager 206 distally moving to be planar with the plane 234. As such, the second engager 206 may disengage the rod 204.

As a force upon the trigger 216 is reduced or substantially eliminated (e.g., as a result of a human operator letting go on the trigger 216), the first compression spring 214 may act upon the first engager 202 to push the trigger 216 back to an initial position, where the trigger 216 is pivoted proximally out away from the handle 212, similar to the same components of the medical dispensing device 10 discussed above. Further, the second engager 206 may be configured to move to an actuated position as the force upon the trigger is reduced or substantially eliminated. The actuated position of the second engager 206 may be substantially similar to the initial position of FIG. 8. In some examples, the second engager 206 is configured to move to an actuated position by a second compression spring 240 that is providing a proximal force upon the second engager 206. In other examples, the second engager 206 is configured to move to an actuated position by being configured to bend back to an initial position. For example, the second engager 206 may be configured to move distally by bending about a pivot point 242 as a result of the force from the absorbing member 230 as described herein, such that upon a reduction or elimination of said force the second engager 206 "unbends" to return to a prior shape.

As the second engager 206 moves axially towards the proximal portion 222 of the housing 210 in response to the reduction or elimination of force upon the trigger 216, the second engager 206 re-engages the rod 204. Upon re-engaging the rod 204, the second engager 206 limits axial movement of the rod 204 towards the proximal portion 222 of the housing 210. This may result, upon full actuation of the medical dispensing device 200 (e.g., full depression of the trigger 216 into the handle 212), in the rod 204 moving distally a predetermined distance that may equate to the amount of distance that the first engager 202 distally moves. Release of the force upon the trigger may result in the rod 204 moving proximally a predetermined distance that may equate to the amount of distance the second engager 206 proximally moves before engaging the rod 204. Together, this configuration may result in the medical dispensing device 200 moving the rod 204 distally a predetermined first amount upon fully actuating the trigger 216 and then moving the rod proximally a predetermined second amount upon releasing the trigger 216, wherein the second amount is smaller than the first amount.

Figure 13:
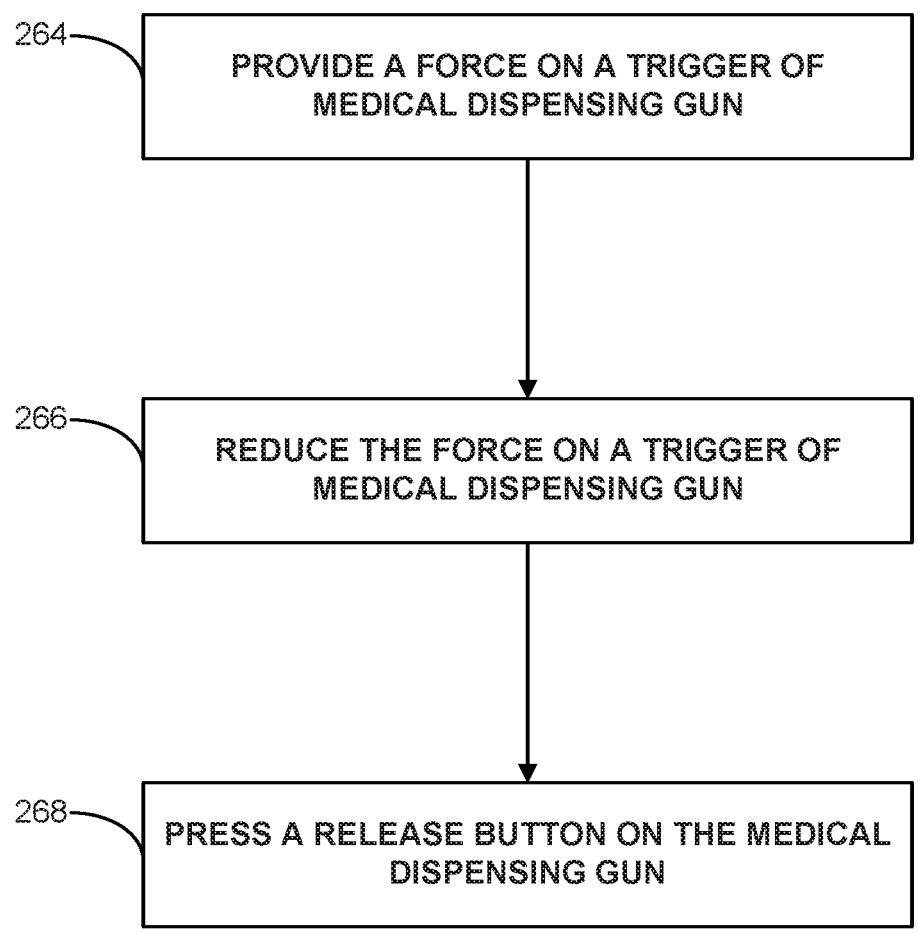
FIG. 13 depicts an example method of using an example medical dispensing device.

FIG. 13 depicts an example method of using an example medical dispensing device 10. Although the medical dispensing device 10 is primarily referred to throughout the description of FIG. 13, in other examples, the method may be used with another medical dispensing device described herein, such as medical dispensing devices 150, 200. It is to be understood that the order of steps within method is for purposes of example only; in other examples, steps of method may be completed in an alternate order or skipped entirely.

Prior to beginning the method shown in FIG. 13, a user may modify a medical dispensing device 10, e.g., to accommodate the particular medical procedure with which the medical dispensing device 10 is used. The user may modify the device 10 by, for example, switching which components are in a medical dispensing device 10 or moving where the components are located within the medical dispensing device 10. In some examples, modifying a medical dispensing device 10 may include determining a specific second engager 16 to use within the medical dispensing device 10. Different second engagers 16 may have different slots 36 that define different amounts that a rod 14 may axially move when actuated. By switching a specific second engager 16 with a respective slot 36 of a first width 72 with another second engager 16 with a respective slot 36 of a second width 72, a respective medical dispensing device 10 may be configured to move a rod 14 a different distance upon actuating a trigger 26. The distance the rod 14 moves in response to the actuation of the trigger 26 may affect the amount of medical substance dispensed from the material reservoir connected to the distal portion of the device 10.

In addition to or instead of modifying the second engager 16 of the device 10, modifying a medical dispensing device 10 may include determining a location or width of a distal hard stop 44 for a first engager 12. Certain frames 18 of a medical dispensing device 10 may enable for a distal hard stop 44 for a first engager 12 to be inserted and removed from a medical dispensing device 10, and positioned at one of a plurality of different positions within the frame 18, therein giving an operator or manufacturer an ability to alter the amount that the rod 14 may axially move when actuated. Determining and therein installing/modifying a medical dispensing device 10 to modify an amount that a rod 14 may axially move may provide performance benefits to the medical dispensing device 10.

In accordance with the technique shown in FIG. 13, a user may apply a force to the trigger 26 of the medical dispensing device 10 (264). The force may need to be equal or greater to a predetermined amount in order to overpower the force of the first compression spring 24 holding the trigger 26 in place using the first engager 12 (e.g., the spring force of the first compression spring as determined by Hooke's law). In some examples, the predetermined amount may be an amount that a human operator can easily provide with a single hand. The force may pivot the trigger 26 into/toward the handle 22, which therein actuates the first engager 12 axially in a distal direction down the housing 20 of the frame 18. The first engager 12 actuating distally down the housing 20 may actuate the rod 14 axially in a distal direction along the housing 20 of the frame 18. The rod 14 may be moved from an initial position of the rod 14.

The force upon the trigger 26 may be maintained (e.g., applied) long enough to engage the second engager 16. The second engager 16 may be engaged through the movement transfer assembly 35. Specifically, a transferring member may axially move the second engager 16 towards a distal portion 45 of the housing 20 of the medical dispensing device 10 once the trigger 26 has pivoted at least a threshold amount. The amount that the second engager 16 axially moves towards a distal portion 45 of the housing 20 may be defined by dimensions of the movement transfer assembly 35 (e.g., the length 72 of the slot 36, the length 186 of the transferring member 168, or the distance 238 between the flange 220 and the plate 228). The second engager 16 may be moved from an initial position. In some examples, the second engager 16 may be configured such that, upon being moved from an initial position, the second engager 16 does not engage the rod 14. In other examples, the second engager 16 may be configured such that, upon being moved from an initial position, the second engager 16 does not limit the proximal movement of the rod 14, even while the second engager 16 still engages the rod 14.

The force upon the trigger 26 may be maintained until the first engager 12 engages a distal hard stop 45. In some examples, all actuation of the medical dispenser device 10 may cease once the first engager 12 engages the distal hard stop 44 for as long as the force is maintained. For example, the distal movement of the rod 14, first engager 12, and second engager 16, as well as the related flexion of the first 24 and/or second compression springs 38 and the rotation of the trigger 26 toward the handle 22, may all cease once the first engager 12 is engaged with the distal hard stop 44.

The user may reduce or substantially eliminate the force applied to the trigger 26 in the direction toward the handle 22 (266). The force may be reduced to below a second predetermined amount which the first compression spring 24 can overcome (e.g., as the second predetermined amount is less than the spring force of the first compression spring, as determined by Hooke's law). Reducing the force to below the second predetermined amount may result in the first compression spring 24 pushing the first engager 12 back against the proximal hard stop 28. As a result of the first engager 12 moving back against the proximal hard stop 28, the trigger 26 may pivot away from the handle 22.

If the force upon the trigger 26 is reduced before the trigger 26 has pivoted at least the threshold amount, then all components of the medical dispensing device 10 may return to an initial position and the second engager 12 may not engage with the rod 14 to limit proximal movement of the rod 14 (e.g., until the rod 14 returns to a respective initial position, at which point the second engager 12 may limit further proximal movement). However, if the force upon the trigger 26 is reduced after the trigger 26 has pivoted at least the threshold amount, then the first engager 12 and the trigger 26 may return to respective initial positions while the second engager 12 moves to the actuated position such that the second engager 16 limits proximal movement once in contact with the rod 14 (e.g., the second engager 16 may hold the rod 14 in a single position relative to the housing 20 once the rod 14 is in the actuated position).

In the example shown in FIG. 13, the user may press the release button 40 (268). The release button 40 may reduce or substantially eliminate forces that retain components of the medical dispensing device 10 in respective resulting positions, enabling a user to return these components to respective initial positions. For example, the release button 40 may reduce or substantially eliminate forces upon both the rod 14 and the second engager 16, enabling a user to grasp and pull the rod 14 and/or second engager 16 back to respective positions that the rod 14 and second engager 16 held before the trigger 26 was initially actuated. In other examples, the medical dispensing device 10 may further contain springs or hard stops to automatically return components to respective initial positions upon the release button 40 being pressed.

Various examples of the disclosure have been described. These and other examples are within the scope of the following claims.

What is claimed is:

1. A medical dispensing device comprising:
    a frame comprising a housing and a handle that extends from a proximal portion of the housing;

a rod positioned within the housing of the frame;

a trigger affixed to the frame and configured to move relative to the handle;

a first engager distal to a first portion of the trigger, wherein the first engager is configured to move distally relative to the housing when the trigger moves axially toward the handle and move proximally relative to the housing when the trigger moves axially away from the handle, wherein the first engager is configured to engage the rod as the first engager moves axially relative to the housing such that the rod undergoes a distal force when the first engager moves distally and the rod undergoes a proximal force when the first engager moves proximally;

a distal hard stop limiting axial rotation of the trigger towards the handle, wherein a maximum distal position of the rod is defined by the distal hard stop;

a compression spring that is engaged with the first engager;

a proximal hard stop limiting axial rotation of the trigger away from the handle, wherein the compression spring presses the first engager into the trigger such that at least one of the trigger or the first engager is configured to rest against the proximal hard stop when the trigger is not actuated;

a second engager that is configured to move axially relative to the housing, wherein the second engager limits proximal movement of the rod when the second engager is in contact with the rod at an actuated position;

a second engager hard stop that defines an actuated position of the second engager relative to the housing;

a movement transfer assembly configured to transfer movement of the trigger to the second engager such that the second engager moves distally when the trigger has moved axially towards the handle more than a threshold amount, wherein the movement transfer assembly includes a transferring member that distally moves the second engager relative to the housing as the trigger moves axially towards the handle after the trigger has moved axially towards the handle more than the threshold amount and until the distal hard stop limits axial rotation of the trigger towards the handle, wherein the second engager is configured to enable the rod to proximally move until the rod is in contact with the second engager while the second engager is at the actuated position.

2. The medical dispensing device of claim 1, wherein the second engager is configured to be in a first position and the rod is configured to be in a second position when the at least one of the trigger or the first engager is resting against the proximal hard stop before the trigger has moved axially towards the handle more than the threshold amount, the medical dispensing device further comprising:

a release button that is configured to substantially eliminate forces that retain the second engager in a position other than the first position and retain the rod in a position other than the second position, enabling both the second engager to return to the first position and the rod to return to the second position.

3. The medical dispensing device of claim 1, wherein the second engager is configured to disengage from the rod when the transferring member distally moves the second engager such that the rod is not in contact with the second engager.

4. The medical dispensing device of claim 3, wherein the second engager is configured to engage the rod in response to the second engager moving proximally following the distal movement of the second engager by the transferring member.

5. The medical dispensing device of claim 1, wherein the trigger is configured to move into contact with the distal hard stop in response to a predetermined force exerted upon the trigger, the trigger being in contact with the distal hard stop resulting in a predetermined amount of distal rod actuation.

6. The medical dispensing device of claim 5, wherein the compression spring is configured to force at least one of the trigger or the first engager to move into contact with the proximal hard stop in response to a termination of the predetermined force upon the trigger, and wherein the second engager is configured to move to the actuated position and the rod is configured to a move a predetermined amount in response to a termination of the predetermined force upon the trigger.

7. The medical dispensing device of claim 1, where a first position of the distal hard stop provides a first maximum distal position of the rod and a second position of the distal hard stop provides a second maximum distal position of the rod.

8. The medical dispensing device of claim 1, further comprising a retaining member that engages the second engager such that the second engager only axially moves towards a distal portion of the housing.

9. The medical dispensing device of claim 8, wherein the transferring member is a tab of a first length extending radially out from the rod, the movement transfer assembly defining a slot of a second length of the second engager configured to receive the tab, the slot configured such that when the tab is received in the slot, a proximal surface of the tab is engaged with a proximal surface of the slot when the at least one of the trigger or the first engager is resting against the proximal hard stop before the trigger moves axially towards the handle more than the threshold amount, wherein a difference of the second length and the first length is substantially similar to the threshold amount such that the trigger rotating axially towards the handle the threshold amount results in a distal surface of the tab engaging a distal surface of the slot such that the proximal surface of the tab no longer engages the proximal surface of the slot, wherein the tab is configured to distally move the second engager as the rod distally moves when the distal surface of the tab is engaged with the distal surface of the slot.

10. The medical dispensing device of claim 9, wherein the medical dispensing device is configured to modify the actuated position of the second engager by being configured to operate another second engager that has another slot of a third length, wherein the third length is different than the second length.

11. The medical dispensing device of claim 1, wherein the compression spring comprises a first compression spring, the movement transfer assembly further including:

a second compression spring engaged with the second engager and configured to press into the second engager to engage the second engager with the second engager hard stop when the second engager is not actuated, wherein the transferring member protrudes proximally into the housing and is configured to move through the housing as the first engager moves axially through the housing, wherein the transferring member does not engage the second engager when the trigger rests against the proximal hard stop, the transferring member being configured to actuate the second engager when the transferring member is moved distally into the housing after the trigger has moved axially towards the handle more than the threshold amount, wherein the transferring member is configured to actuate the second engager by at least exerting a distal force upon the second engager, the distal force being sufficient to overcome the second compression spring holding the second engager against the second engager hard stop such that at least a portion of the second engager moves distally.

12. The medical dispensing device of claim 1, wherein:
the second engager is proximal to the handle,
the trigger is proximal to the handle and is configured to move distally as the trigger moves axially towards the handle and to move proximally as the trigger moves axially away from the handle, and
the movement transfer assembly includes:
  the transferring member extending proximally from the trigger;
  an absorbing member that extends distally from the second engager, wherein the absorbing member includes a flange on a distal edge of the absorbing member; and
  a plate affixed to the transferring member and coupling the transferring member to the absorbing member, wherein the plate defining an opening through which the absorbing member extends, the flange of the absorbing member being larger than the opening, wherein the plate is configured to slide over the absorbing member until the trigger has moved axially towards the handle at least the threshold amount, and to engage the flange upon the trigger rotating axially towards the handle at least the threshold amount such that the distal movement of the transferring member is transferred to both the absorbing member and the second engager.

13. The medical dispensing device of claim 1, wherein the trigger is configured to pivot relative to the handle.

14. A method of dispensing a medical substance, the method comprising:
  actuating a rod distally a first distance to a maximum distal position using a first engager by applying a force upon a trigger of a medical dispensing device, the medical dispensing device comprising:
    a frame comprising a housing and a handle that extends from a proximal portion of the housing;
    the rod positioned within the housing of the frame;
    the trigger affixed to the frame and configured to move relative to the handle;
    the first engager distal to a first portion of the trigger, wherein the first engager moves distally relative to the housing when the trigger moves axially toward the handle and the first engager is configured to move distally relative to the housing when the trigger moves axially toward the handle and move proximally relative to the housing when the trigger moves axially away from the handle, wherein the first engager is configured to engage the rod as the first engager moves axially relative to the housing such that the rod undergoes a distal force when the first engager moves distally and the rod undergoes a proximal force when the first engager moves proximally;
    a distal hard stop limiting axial rotation of the trigger towards the handle, wherein the maximum distal position of the rod is defined by the distal hard stop;
    a compression spring that is engaged with the first engager;
    a proximal hard stop limiting axial rotation of the trigger away from the handle, wherein the compression spring presses the first engager into the trigger such that at least one of the trigger or the first engager is configured to rest against the proximal hard stop when the trigger is not actuated;
    a second engager that is configured to move axially relative to the housing, wherein the second engager limits proximal movement of the rod when the second engager is in contact with the rod at the actuated position;
    a second engager hard stop that defines an actuated position of the second engager relative to the housing; and
    a movement transfer assembly configured to transfer movement of the trigger to the second engager such that the second engager is configured to move distally when the trigger has moved axially towards the handle more than a threshold amount, wherein the movement transfer assembly includes a transferring member that distally moves the second engager relative to the housing as the trigger moves axially towards the handle after the trigger has moved axially towards the handle more than the threshold amount and until the distal hard stop limits axial rotation of the trigger towards the handle, wherein the second engager is configured to enable the rod to proximally move until the rod is in contact with the second engager while the second engager is at the actuated position;
  reducing a force upon the trigger such that at least one of a trigger or a first engager rests against the proximal hard stop, wherein reducing the force upon the trigger results in the rod proximally moving a second distance, wherein the second distance is less than the first distance.

15. The method of claim 14, the method further comprising modifying the maximum distal position of the rod by replacing the distal hard stop with another distal hard stop, where the distal hard stop has a first width and the another distal hard stop has a second width.

16. The method of claim 14, wherein the transferring member is a tab of a first length extending radially out from the rod, wherein the movement transfer assembly defines a slot of a second length of the second engager configured to receive the tab, the slot configured such when the tab is received in the slot, a proximal surface of the tab is engaged with a proximal surface of the slot when the at least one of the trigger or the first engager is resting against the proximal hard stop before the trigger moves axially towards the handle more than the threshold amount, wherein a difference of the second length and the first length is substantially similar to the threshold amount such that the trigger rotating axially towards the handle the threshold amount results in a distal surface of the tab engaging a distal surface of the slot such that the proximal surface of the tab no longer engages the proximal surface of the slot, wherein the tab is configured to distally move the second engager as the rod distally moves when the distal surface of the tab is engaged with the distal surface of the slot.

17. The method of claim 16, the method further comprising modifying the actuated position of the second engager by replacing the second engager with another second engager that has another slot of a third length, wherein the third length is different than the second length.

18. The method of claim 14, wherein the compression spring comprises a first compression spring, wherein the movement transfer assembly includes:
- a second compression spring that is engaged with the second engager and configured to press into the second engager to engage the second engager with the second engager hard stop when the second engager is not actuated,
- wherein the transferring member protrudes proximally into the housing and is configured to move through the housing as the first engager moves axially through the housing, wherein the transferring member does not engage the second engager when the trigger rests against the proximal hard stop and moves axially through the housing as the first engager moves axially through the housing, the transferring member being configured to actuate the second engager when the transferring member is moved distally into the housing after the trigger has moved axially towards the handle more than the threshold amount, wherein the transferring member is configured to actuate the second engager by at least exerting a distal force upon the second engager, the distal force being sufficient to overcome the second compression spring holding the second engager against the second engager hard stop such that at least a portion of the second engager moves distally.

19. The method of claim 14, wherein:
the second engager is proximal to the handle,
the trigger is proximal to the handle and is configured to move distally as the trigger moves axially towards the handle and to move proximally as the trigger moves axially away from the handle, and
the movement transfer assembly includes:
- the transferring member extending proximally from the trigger;
- an absorbing member that extends distally from the second engager, wherein the absorbing member includes a flange on a distal edge of the absorbing member; and
- a plate affixed to the transferring member and coupling the transferring member to the absorbing member, wherein the plate defining an opening through which the absorbing member extends, the flange of the absorbing member being larger than the opening,
- wherein the plate is configured to slide over the absorbing member until the trigger has moved axially towards the handle at least the threshold amount, and to engage the flange upon the trigger rotating axially towards the handle at least the threshold amount such that the distal movement of the transferring member is transferred to both the absorbing member and the second engager.

20. A medical dispensing device for dispensing materials by actuating a rod distally toward a material reservoir, the medical dispensing device comprising:
- a frame comprising a housing that houses the rod and a handle that extends from a proximal portion of the housing;
- a trigger affixed to the frame and configured to pivot axially about a pivot point towards and away from the handle;
- a distal hard stop limiting axial rotation of the trigger towards the handle;
- a first engager that is configured immediately distal to a first portion of the trigger, wherein the first engager moves distally relative to the housing when the trigger pivots axially toward the handle and the first engager moves proximally relative to the housing when the trigger pivots axially away from the handle, wherein the first engager is configured to engage the rod as the first engager moves axially relative to the housing such that the rod undergoes a distal force when the first engager moves distally and the rod undergoes a proximal force when the first engager moves proximally;
- a second engager that is configured to move axially relative to the housing, wherein the second engager limits proximal movement of the rod when the second engager is in contact with the rod at an actuated position of the second engager; and
- means for absorbing and transferring movement of the trigger onto the second engager such that the second engager only moves if the trigger has pivoted axially towards the handle more than a threshold amount, wherein the means for absorbing and transferring movement of the trigger onto the second engager distally moves the second engager along the housing as the trigger pivots axially towards the handle after the trigger has pivoted axially towards the handle more than a threshold amount and until the distal hard stop limits axial rotation of the trigger towards the handle, wherein the means for absorbing and transferring movement of the trigger onto the second engager defines both a maximum distal position of the rod and the actuated position of the second engager.

21. The medical dispensing device of claim 20, means for absorbing and transferring movement of the trigger onto the second engager results in overpressurization of forces upon the rod as the rod axially moves to the maximum distal position.

* * * * *